(12) United States Patent
Cox et al.

(10) Patent No.: US 7,259,154 B2
(45) Date of Patent: Aug. 21, 2007

(54) PYRROLOPYRIMIDINES

(75) Inventors: Paul Joseph Cox, Flemington, NJ (US); Tahir Nadeem Majid, Hoboken, NJ (US); Stephanie Daniele Deprets, Paris (FR); Shelley Amendola, Bedminster, NJ (US); Iain McFarlane McLay, Loughton (GB); Christopher Edlin, Hitchin (GB); David John Aldous, Gillette, NJ (US); Brian Pedgrift, Flemington, NJ (US); Frank Halley, Chaville (FR); Michael Edwards, Morristown, NJ (US); Bernard Baudoin, Chaville (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/744,478

(22) Filed: Dec. 23, 2003

(65) Prior Publication Data

US 2004/0142947 A1  Jul. 22, 2004

Related U.S. Application Data

(63) Continuation of application No. PCT/GB02/02835, filed on Jun. 21, 2002.

(60) Provisional application No. 60/301,678, filed on Jun. 28, 2001.

(30) Foreign Application Priority Data

Jun. 23, 2001  (GB) ................................. 0115393.1

(51) Int. Cl.
| | |
|---|---|
| *C07D 413/04* | (2006.01) |
| *C07D 487/04* | (2006.01) |
| *A61P 11/06* | (2006.01) |
| *A61K 31/5355* | (2006.01) |
| *A61K 31/519* | (2006.01) |
| *A61K 31/66* | (2006.01) |
| *C07F 9/38* | (2006.01) |

(52) U.S. Cl. .................. 514/75; 514/234.2; 514/265.1; 544/117; 544/280; 544/243

(58) Field of Classification Search ............. 514/234.2, 514/265.1, 75; 544/117, 280, 243
See application file for complete search history.

(56) References Cited

U.S. PATENT DOCUMENTS

| | | | |
|---|---|---|---|
| 6,001,839 A | 12/1999 | Calderwood et al. | |
| 6,140,317 A | 10/2000 | Traxler et al. | |
| 6,627,754 B2 | 9/2003 | Blumenkopf et al. | |
| 6,635,762 B1 | 10/2003 | Blumenkopf et al. | |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Noble, M.E.M. et al, Science, vol. 303, 2004, pp. 1800-1805.*
Yamamoto, N. et al, J Pharmacol Exp Ther. Sep. 2003;306(3):1174-81. Epub May 23, 2003.*
Wedge, S.R. et al, Cancer Research 60, 970-975, Feb. 15, 2000.*
David J.W. Grant, "University of Minnesota—Twin Cities Campus College of Pharmacy, Annual Report", [online] 1999, [retrieved on Feb. 13, 2003]. Retrieved from the internet, <http://www.msi.umn.edu/general/Reports/ar99/departments/pharmacy.html>.*
Vippagunta, S. R. et al, Advanced Drug Delivery Reviews, 48, pp. 3-26, 2001.*
Bergstrom, et al., Palladium-mediated synthesis of C-5 pyrimidine nucleoside thioethers from disulfides and mercurlnucleosides, J. Org. Chem.; 56(19; 1991; pp. 5588-5602.

* cited by examiner

*Primary Examiner*—Mark L. Berch
*Assistant Examiner*—Susanna Moore
(74) *Attorney, Agent, or Firm*—James W. Bolcsak

(57) ABSTRACT

Compounds of the formula

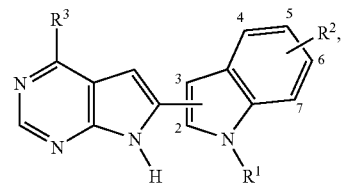

and N-oxides, prodrugs, acid bioisosteres, pharmaceutically acceptable salts or solvates of such compounds, or N-oxides, prodrugs, or acid bioisosteres of such salts or solvates, to compositions comprising such compounds, and methods of treatment comprising administering, to a patient in need thereof, such compounds and compositions.

16 Claims, No Drawings

PYRROLOPYRIMIDINES

CROSS REFERENCE TO RELATED APPLICATION

This application is a national phase continuation of International Patent Application No. PCT/GB02/02835, filed Jun. 21, 2002, which claims benefit of Great Britian application No. GB0115393.1, filed Jun. 23, 2001 and U.S. provisional application No. 60/301,678, filed Jun. 28, 2001.

FIELD OF THE INVENTION

This invention is directed to substituted pyrrolopyrimidines, their preparation, pharmaceutical compositions containing these compounds, and their pharmaceutical use in the treatment of disease states capable of being modulated by the inhibition of the protein kinases.

BACKGROUND OF THE INVENTION

Protein kinases participate in the signalling events which control the activation, growth and differentiation of cells in response to extracellular mediators and to changes in the environment. In general, these kinases fall into several groups; those which preferentially phosphorylate serine and/or threonine residues and those which preferentially phosphorylate tyrosine residues [S. K. Hanks and T. Hunter, FASEB. J., 1995, 9, pages 576-596]. The serine/threonine kinases include for example, protein kinase C isoforms [A. C. Newton, J. Biol. Chem., 1995, 270, pages 28495-28498] and a group of cyclin-dependent kinases such as cdc2 [J. Pines, Trends in Biochemical Sciences, 1995, 18, pages 195-197]. The tyrosine kinases include membrane-spanning growth factor receptors such as the epidermal growth factor receptor [S. Iwashita and M. Kobayashi, Cellular Signalling, 1992, 4, pages 123-132], and cytosolic non-receptor kinases such as p56tck, p59fYn, ZAP-70 and csk kinases [C. Chan et. al., Ann. Rev. Immunol., 1994, 12, pages 555-592].

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect.

Syk is a 72-kDa cytoplasmic protein tyrosine kinase that is expressed in a variety of hematopoietic cells and is an essential element in several cascades that couple antigen receptors to cellular responses. Thus, Syk plays a pivotal role in signalling of the high affinity IgE receptor, FcεR1, in mast cells and in receptor antigen signalling in T and B lymphocytes. The signal transduction pathways present in mast, T and B cells have common features. The ligand binding domain of the receptor lacks intrinsic tyrosine kinase activity. However, they interact with transducing subunits that contain immunoreceptor tyrosine based activation motifs (ITAMs) [M. Reth, Nature, 1989, 338, pages 383-384]. These motifs are present in both the β and γ subunits of the FcεR1, in the ξ-subunit of the T cell receptor (TCR) and in the IgGα and IgG β subunits of the B cell receptor (BCR). [N. S. van Oers and A. Weiss, Seminars in Immunology, 1995, 7, pages 227-236] Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SH2-mediated association of Syk with an activated receptor stimulates Syk kinase activity and localises Syk to the plasma membrane.

In Syk deficient mice, mast cell degranulation is inhibited, suggesting that this is an important target for the development of mast cell stabilising agents [P. S. Costello, Oncogene, 1996, 13, pages 2595-2605]. Similar studies have demonstrated a critical role for Syk in BCR and TCR signalling [A. M. Cheng, Nature, 1995, 378, pages 303-306, (1995) and D. H. Chu et al., Immunological Reviews, 1998, 165, pages 167-180]. Syk also appears to be involved in eosinophil survival in response to IL-5 and GM-CSF [S. Yousefi et al., J. Exp. Med., 1996, 183, pages 1407-1414]. Despite the key role of Syk in mast cell, BCR and T cell signalling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors [M. Ishiai et al., Immunity, 1999, 10, pages 117-125 and L. R. Hendricks-Taylor et al., J. Biol. Chem., 1997, 272, pages 1363-1367]. In addition Syk appears to play an important role in the CD40 signalling pathway, which plays an important role in B cell proliferation [M. Faris et al., J. Exp. Med., 1994, 179, pages 1923-1931].

Syk is further involved in the activation of platelets stimulated via the low-affinity IgG receptor (Fc gamma-RIIA) or stimulated by collagen [F. Yanaga et al., Biochem. J., 1995, 311, (Pt. 2) pages 471-478].

Focal adhesion kinase (FAK) is a non-receptor tyrosine kinase involved in integrin-mediated signal transduction pathways. FAK colocalizes with integrins in focal contact sites and FAK activation and its tyrosine phosphorylation have been shown in many cell types to be dependent on integrins binding to their extracellular ligands. Results from several studies support the hypothesis that FAK inhibitors could be useful in cancer treatment. For example, FAK-deficient cells migrate poorly in response to chemotactic signals and overexpression of C-terminal domain of FAK blocks cell spreading as well as chemotactic migration (Sieg et al, J. Cell Science, 1999, 112, 2677-2691; Richardson A. and Parsons T., Cell, 1997, 97, 221-231); in addition, tumor cells treated with FAK antisense oligonucleotides lost their attachment and underwent apoptosis (Xu et al, Cell Growth Differ. 1996, 4, 413-418). FAK has been reported to be overexpressed in prostate, breast, thyroid, colon and lung cancers. The level of expression of FAK is directly correlated with tumors demonstrating the most aggressive phenotype.

Angiogenesis or the formation of new blood vessels by sprouting from the preexisting vasculature is of central importance for embryonic development and organogenesis. Abnormal enhanced neovascularization is observed in rheumatoid arthritis, diabetic retinopathy and during tumor development (Folkman, Nat. Med., 1995, 1, 27-31.). Angiogenesis is a complex multistage process which includes activation, migration, proliferation and survival of endothelial cells. Extensive studies in the field of tumor angiogenesis in the past two decades have identified a number of therapeutic targets including kinases, proteases and integrins resulting in the discovery of many new anti-angiogenic agents, including KDR inhibitors some of which are currently under clinical evaluation (Jekunen, et al Cancer Treatment Rev. 1997, 23, 263-286.). Angiogenesis inhibitors may be used in frontline, adjuvant and even preventive settings for the emergence or regrowth of malignancies.

Several proteins involved in chromosome segregation and spindle assembly have been identified in yeast and *drosophila*. Disruption of these proteins results in chromosome missegregation and monopolar or disrupted spindles. Among these kinases are the Ip11 and aurora kinases from *S. cerevisiae* and *drosophila* respectively, which are required for centrosome separation and chromosome segregation. One human homologue of yeast Ip11 was recently cloned and characterized by different laboratories. This kinase termed Aurora2, STK15 or BTAK belongs to the serine/threonine kinase family. Bischoff et al showed that Aurora2 is oncogenic and is amplified in human colorectal cancers (EMBO J, 1998, 17, 3052-3065). It has also been exemplified in cancers involving epithelial tumors such as breast cancer.

SUMMARY OF THE INVENTION

This invention concerns substituted pyrrolopyrimidines of formula (I), which have the ability to inhibit one or more protein kinases, more particularly, FAK, KDR, Syk kinase or Aurora2, especially Syk kinase.

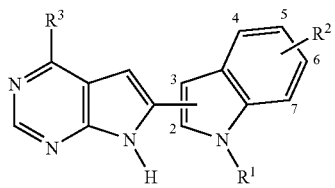

(I)

wherein $R^1$ represents hydrogen, —C(=O)—$NY^1Y^2$, —C(=O)—$OR^5$, —$SO_2$—$NY^1Y^2$, —$SO_2$—$R^7$, —C(=O)$R^7$, or $R^1$ may be alkenyl, alkenyloxy, alkyl, alkynyl, aryl, heteroaryl, heterocycloalkyl, cycloalkyl or cycloalkylalkyl, each optionally substituted by one or more groups selected from aryl, cycloalkyl, cyano, halo, heteroaryl, heterocycloalkyl, —CHO (or a 5-, 6- or 7-membered cyclic acetal derivative thereof), —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—$SO_2$—$R^7$, —N($R^6$)—$SO_2$—$NY^3Y^4$, —$OR^7$, —C(=O)—$R^7$, hydroxy, alkoxy and carboxy;

$R^2$ represents one or more groups selected from hydrogen, acyl, alkylenedioxy, alkenyl, alkenyloxy, alkynyl, aryl, cyano, halo, hydroxy, heteroaryl, heterocycloalkyl, nitro, $R^4$, —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—C(=O)—$OR^7$, —N($R^6$)—$SO_2$—$R^7$, —N($R^6$)—$SO_2$—$NY^3Y^4$, —$SO_2$—$NY^1Y^2$ and —$ZR^4$;

$R^3$ represents H, cyano, halo, hydroxy, nitro, $R^4$, $NY^1Y^2$, —$ZR^4$, —C(=O)—$OR^5$, —C(=O)—$R^7$, —C(=O)—$NY^1Y^2$, —N($R^8$)—C(=O)—$R^4$, —N($R^8$)—C(=O)—$NY^1Y^2$, —N($R^8$)—C(=O)—$OR^5$, —$SO_2$—$NY^3NY^4$, or —N($R^8$)—$SO_2$—$R^7$, or $R^3$ represents aryl, heteroaryl, alkenyl or alkynyl, each optionally substituted by one or more groups selected from aryl, cyano, halo, hydroxy, heteroaryl, heterocycloalkyl, nitro, —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—C(=O)—$OR^7$, —N($R^6$)—$SO_2$—$R^7$, —N($R^6$)—$SO_2$—$NY^3Y^4$, —$SO_2$—$NY^1Y^2$ or —$ZR^4$;

$R^4$ represents alkyl, cycloalkyl or cycloalkylalkyl each optionally substituted by one or more groups selected from aryl, cycloalkyl, cyano, halo, heteroaryl, heterocycloalkyl, hydroxy, —CHO (or a 5-, 6- or 7-membered cyclic acetal derivative thereof), —C(=O)—$NY^1Y^2$, —C(=O)—$OR^5$, —$NY^1Y^2$, —N($R^6$)—C(=O)—$R^7$, —N($R^6$)—C(=O)—$NY^3Y^4$, —N($R^6$)—$SO_2$—$R^7$, —N($R^6$)—$SO_2$—$NY^3Y^4$, —$OR^7$ and —C(=O)—$R^7$; $R^4$ can also be optionally interspersed with a group selected from O, S(O)$_n$, N$R^6$;

$R^5$ represents hydrogen, alkyl, alkenyl, aryl, arylalkyl, heteroaryl or heteroarylalkyl;

$R^6$ represents hydrogen or lower alkyl;

$R^7$ represents alkyl, aryl, arylalkyl, cycloalkyl, cycloalkylalkyl, heteroaryl, heteroarylalkyl, heterocycloalkyl or heterocycloalkylalkyl;

$R^8$ represents hydrogen or lower alkyl;

$Y^1$ and $Y^2$ are independently hydrogen, alkenyl, aryl, cycloalkyl, heteroaryl or alkyl optionally substituted by one or more groups selected from aryl, halo, heteroaryl, hydroxy, —C(=O)—$NY^3Y^4$, —C(=O)—$OR^5$, —$NY^3Y^4$, —N($R^6$)—C(=O)—$R^7$, —N($R^6$)—C(=O)—$NY^3Y^4$, —N($R^6$)—$SO_2$—$R^7$, —N($R^6$)—$SO_2$—$NY^3Y^4$ and —$OR^7$; or the group —$NY^1Y^2$ may form a cyclic amine;

$Y^3$ and $Y^4$ are independently hydrogen, alkenyl, alkyl, aryl, arylalkyl, cycloalkyl, heteroaryl or heteroarylalkyl; or the group —$NY^3Y^4$ may form a cyclic amine;

Z represents O or S(O)$_n$;

n is zero or an integer 1 or 2;

and their corresponding N-oxides, and their prodrugs, and their acid bioisosteres; and pharmaceutically acceptable salts and solvates (e.g. hydrates) of such compounds and their N-oxides and their prodrugs, and their acid bioisosteres; together with one or more pharmaceutically acceptable carriers or excipients.

DETAILED DESCRIPTION OF THE INVENTION

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21,p283 "Bioisosterism In Drug Design"; Yun, Hwahak Sekye, 1993, 33, pages 576-

579 "Application Of Bioisosterism To New Drug Design"; Zhao, Huaxue Tongbao, 1995, pages 34-38 "Bioisosteric Replacement And Development Of Lead Compounds In Drug Design"; Graham, Theochem, 1995, 343, pages 105-109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched," as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain, which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" is an alkenyl-O— group wherein alkenyl is as defined above. Exemplary alkenyloxy groups include allyloxy.

"Alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched chain having about 1 to about 15 carbon atoms in the chain, optionally substituted by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be a straight or branched chain having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl. Exemplary alkyl groups substituted by one or more halogen atoms include trifluoromethyl.

"Alkylene" means an aliphatic bivalent; radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-SO$_2$— group in which the alkyl group is as previously described. Preferred alkylsulfonyl groups are those in which the alkyl group is $C_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which group may be a straight or branched chain having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, halo, heteroaroyl, heteroaryl, heteroarylalkyloxy, heteroaroylamino, heteroaryloxy, hydroxy, nitro, trifluoromethyl, —NY$^3$Y$^4$, —CONY$^3$Y$^4$, —SO$_2$NY$^3$Y$^4$, —NY$^3$—C(=O)alkyl, —NY$^3$SO$_2$alkyl or alkyl optionally substituted with aryl, heteroaryl, hydroxy, or —NY$^3$Y$^4$.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are selected from carbon, oxygen, sulfur, and nitrogen. Examples of azaheteroaryl groups include benzimidazolyl, imidazolyl, indazolinyl, indolyl, isoquinolinyl, pyridyl, pyrimidinyl, pyrrolyl, quinolinyl, quinazolinyl and tetrahydroindolizinyl.

"Cyclic amine" means a 3 to 8 membered monocyclic cycloalkyl ring system wherein one of the ring carbon atoms is replaced by nitrogen and which (i) may also contain a further heteroatom-containing group selected from O, S, $SO_2$, or $NY^5$ (where $Y^5$ is hydrogen, alkyl, aryl, arylalkyl, —C(=O)—$R^7$, —C(=O)—$OR^7$ or —$SO_2R^7$); and (ii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinoline and the like groups.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl and cycloheptenyl.

"Cycloalkyl" means a saturated monocyclic or bicyclic ring system of about 3 to about 10 carbon atoms, optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro and chloro.

"Heteroaroyl" means a heteroaryl-C(=O)— group in which the heteroaryl group is as described herein. Exemplary heteroaryl groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups, optionally substituted by one or more "aryl group substituents" as defined above, except where otherwise defined). Optional substituents include one or more "aryl group substituents" as defined above, except where otherwise defined.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy. "Heteroarylsulfonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms or heteroatom-containing groups selected from O, S and $NY^5$ and mat be optionally substituted by oxo; (ii) a partially saturated multicyclic heterocarbocyclic moiety in which an aryl (or heteroaryl) ring, each optionally substituted by one or more "aryl group substituents," and a heterocycloalkyl group are fused together to form a cyclic structure. (Examples of such groups include chromanyl, dihydrobenzofuranyl, indolinyl and pyrindolinyl groups).

"Heterocycloalkylalkyl" means a heterocycloalkyl-alkyl- group in which the heterocycloalkyl and alkyl moieties are as previously described.

"Prodrug" means a compound which is convertible in vivo by metabolic means (e.g. by hydrolysis) to a compound of formula (I), including N-oxides thereof. For example an ester of a compound of formula (1) containing a hydroxy group may be convertible by hydrolysis in vivo to the parent molecule. Alternatively, an ester of a compound of formula (I) containing a carboxy group may be convertible by hydrolysis in vivo to the parent molecule.

Suitable esters of compounds of formula (I) containing a hydroxy group are, for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group are, for example, those described by F. J. Leinweber, Drug Metab. Res., 1987, 18, page 379.

Suitable esters of compounds of formula (I) containing both a carboxy group and a hydroxy group within the moiety —$L^1$—Y include lactones formed by loss of water between said carboxy and hydroxy groups. Examples of such lactones include caprolactones and butyrolactones.

An especially useful class of esters of compounds of formula (I), containing a hydroxy group, may be formed from acid moieties selected from those described by Bundgaard et. al., J. Med. Chem., 1989, 32, page 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, orginine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-beta-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent:
(i) hydrogen
(ii) $C_{1-4}$alkyl [e.g. —$CH_3$ or —$CH_2CH_3$];
(iii) $C_{1-4}$alkyl substituted by halo [e.g. —$CH_2CF_3$];
(iv) $C_{1-4}$alkyl substituted by hydroxy [e.g. —$CH_2OH$, —$CH_2CH_2OH$ or —$CH_2CH_2CH_2OH$];
(v) $C_{1-4}$alkyl substituted by —$N(R^6)C(=O)$—$R^7$ [e.g. —$CH_2CH_2CH_2NHC(=O)CH_3$]
(vi) $C_{1-4}$alkyl substituted by —$C(=O)$—$NY^1Y^2$ [e.g.

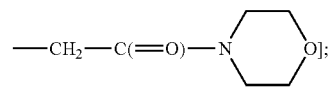

or
(vii) cycloalkylalkyl substituted by hydroxy [e.g.

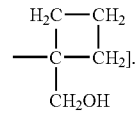

Compounds of formula (I) in which $R^1$ represents hydrogen, —$CH_3$, —$CH_2CH_3$, —$CH_2CF_3$ or

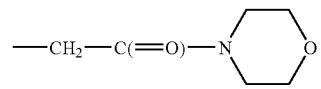

are especially preferred. $R^1$ more especially represents hydrogen.

$R^2$ may particularly represent:
(i) carboxy or an acid bioisostere (e.g.

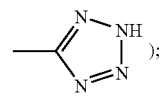

(ii) hydroxy;
(iii) alkyl substituted by carboxy [e.g. —$CH_2CH_2CO_2H$];
(iv) heteroaryl [e.g.

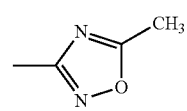

or pyridyl];
(v) —$OR^4$ in which $R^4$ is alkyl [e.g. —$OCH_3$];
(vi) —$OR^4$ in which $R^4$ is alkyl or cycloalkylalkyl substituted by one or more hydroxy groups [e.g. —$OCH_2CH_2OH$, —$OCH_2CH_2CH_2OH$, —$OCH(CH_3)CH_2OH$, —$OCH_2CH(OH)CH_3$,

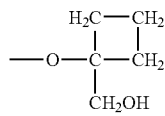

or —OCH$_2$CH(OH)CH$_2$OH];

(vii) —OR$^4$ in which R$^4$ is alkyl substituted by one or more alkoxy groups [e.g. —OCH(CH$_3$)CH$_2$OCH$_3$];

(viii) —OR$^4$ in which R$^4$ is alkyl or cycloalkyl substituted by one or more carboxy groups [e.g. —OCH$_2$CO$_2$H, —OCH(CH$_3$) CO$_2$H or

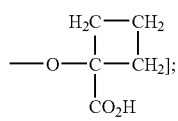

];

(ix) —OR$^4$ in which R$^4$ is cycloalkyl substituted by —C(=O)—NY$^1$Y$^2$ [e.g.

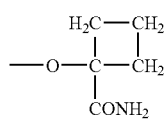

or

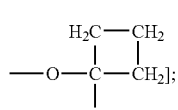

];

(x) —C(=O)—R in which R is alkyl [e.g. —C(=O)—CH$_3$];

(xi) —C(=O)—NY$^1$Y$^2$ [e.g. —CONH$_2$, —CONHCH$_3$, —CONHCH(CH$_2$OH)$_2$, —CONHCH$_2$CH$_2$OH, —CONHC(CH$_3$)$_2$CH$_2$OH, —CONHCH$_2$CH$_2$OCH$_3$, —CONHCH$_2$CH$_2$CONH$_2$, —CONHCH$_2$C(CH$_3$)$_2$OH or

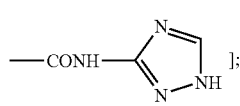

];

(xii) —N(R$^6$)—C(=O)—R$^7$ [e.g. —NHC(=O)CH$_3$].

Compounds of formula (I) in which R$^2$ represents —OCH$_3$ or —CONHC(CH$_3$)$_2$ CH$_2$OH are especially preferred. R$^2$ more especially represents —OCH$_3$.

R$^3$ may particularly represent:
(i) hydrogen;
(ii) cyano;
(iii) optionally substituted aryl (e.g. phenyl);
(iv) optionally substituted heteroaryl (e.g. optionally substituted pyridyl or optionally substituted indolyl, especially

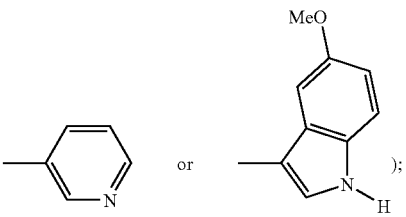

);

(v) alkyl (e.g. methyl or ethyl);
(vi) alkyl substituted by one or more halogen atoms (e.g. trifluoromethyl);
(vii) alkyl substituted by —C(=O)—NY$^1$Y$^2$, especially —CH$_2$—CH$_2$—C(=O)NHCH$_3$;
(viii) alkyl substituted by —OR$^7$ (e.g. —CH$_2$—CH$_2$—OCH$_3$);
(ix) —ZR$^4$, especially —OCH$_3$, —OCH$_2$CH$_3$, —OCF$_2$H or —OCH$_2$—CH$_2$—OCH$_3$;
(x) —C(=O)—OR$^5$, especially —C(=O)—OH;
(xi) —C(=O)—NY$^1$Y$^2$, especially —C(=O)NHCH$_3$ or —C(=O)—NH—C(CH$_3$)$_2$—CH$_2$OH; and
(xii) —NY$^1$Y$^2$, especially

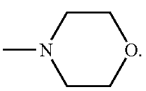

Compounds of formula (I) in which R$^3$ represents hydrogen, cyano, pyridyl, trifluoromethyl, —CH$_2$—CH$_2$—C(=O)NHCH$_3$, —OCF$_2$H, —C(=O)—NH—C(CH$_3$)$_2$—CH$_2$OH or

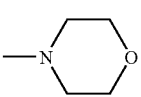

are especially preferred. R$^3$ more especially represents —OCH$_3$.

R$^2$ is preferably attached to position 5 of the indole ring.

The group

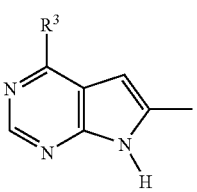

is preferably attached to the 3 position of the indole ring

It is to be understood that this invention covers all appropriate combinations of the particular and preferred groupings referred to herein.

Particular preferred compounds of the invention are:
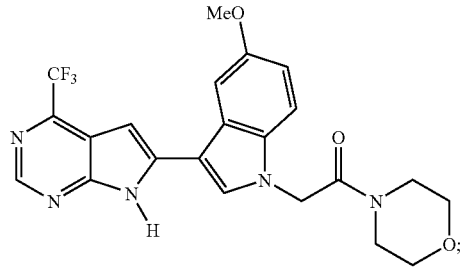
(II)
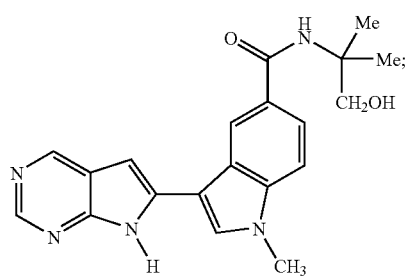
(III)
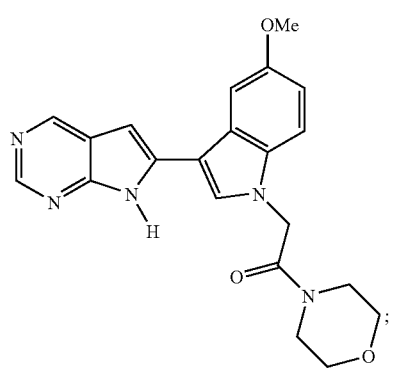
(IV)
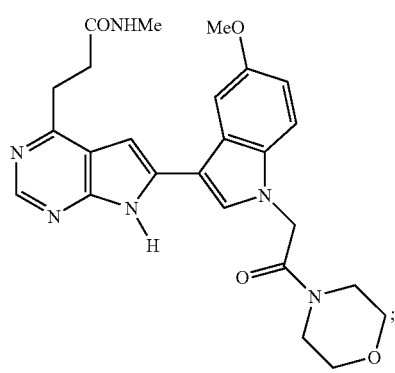
(V)
-continued
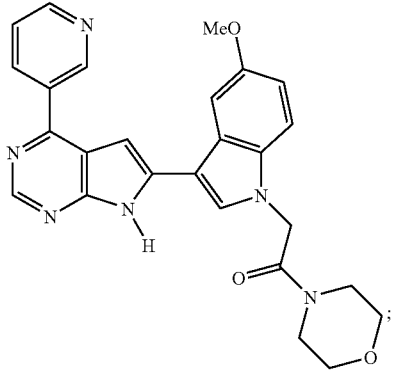
(VI)
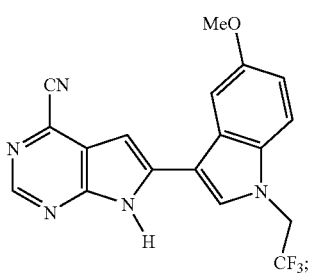
(VII)
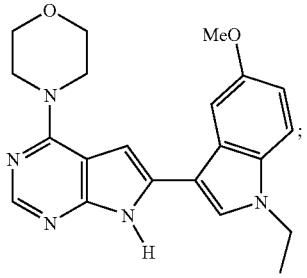
(VIII)
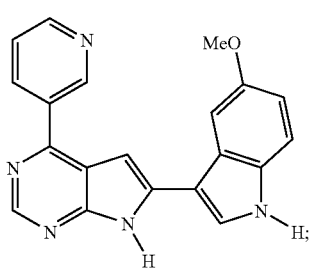
(IX)
(X)

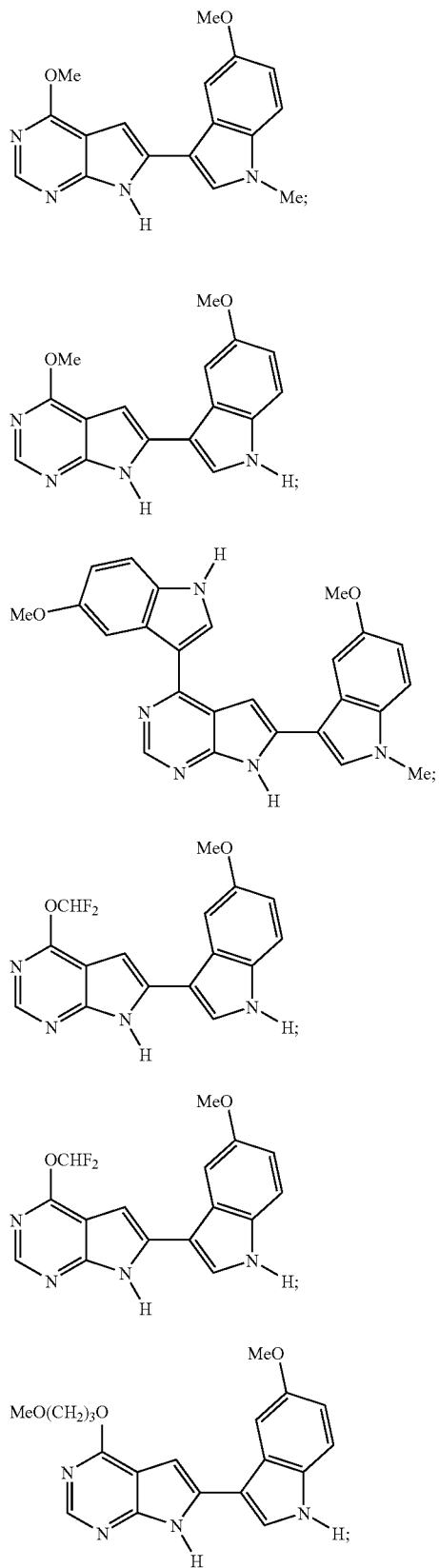
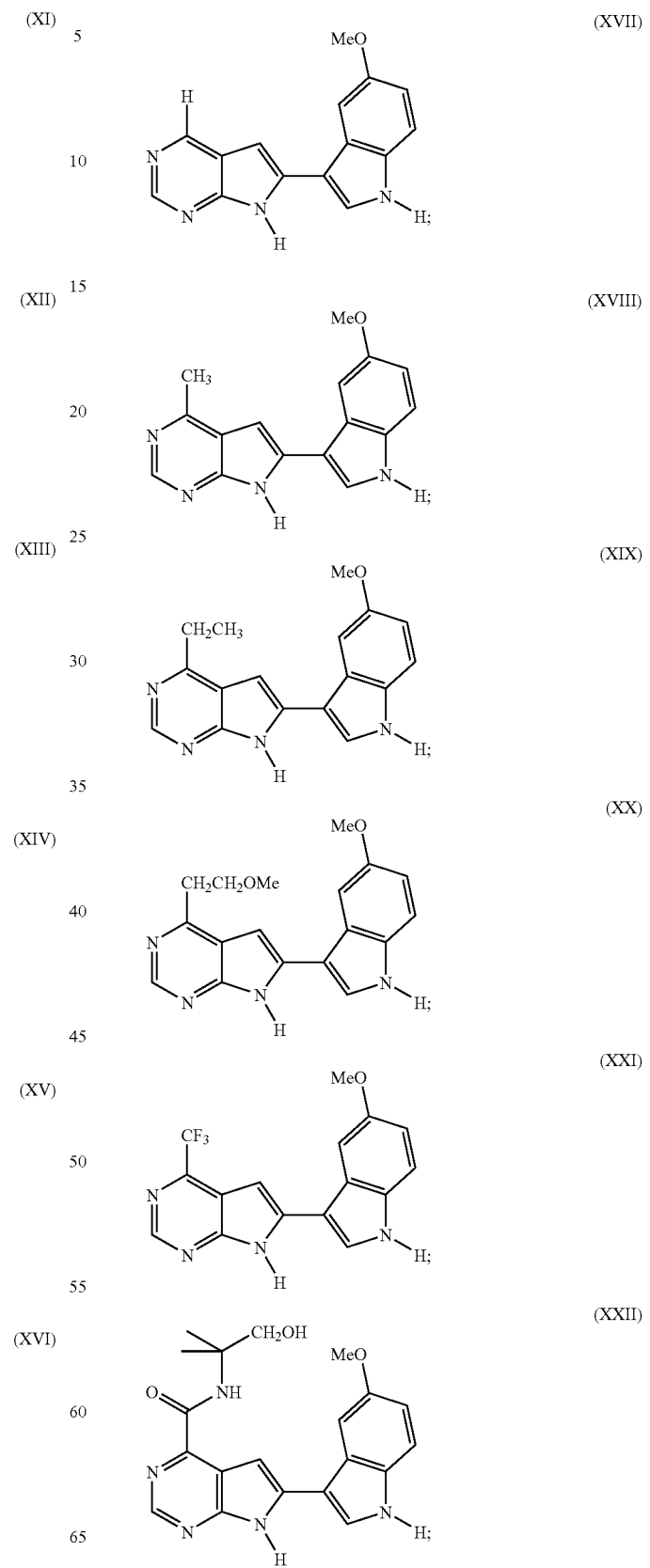

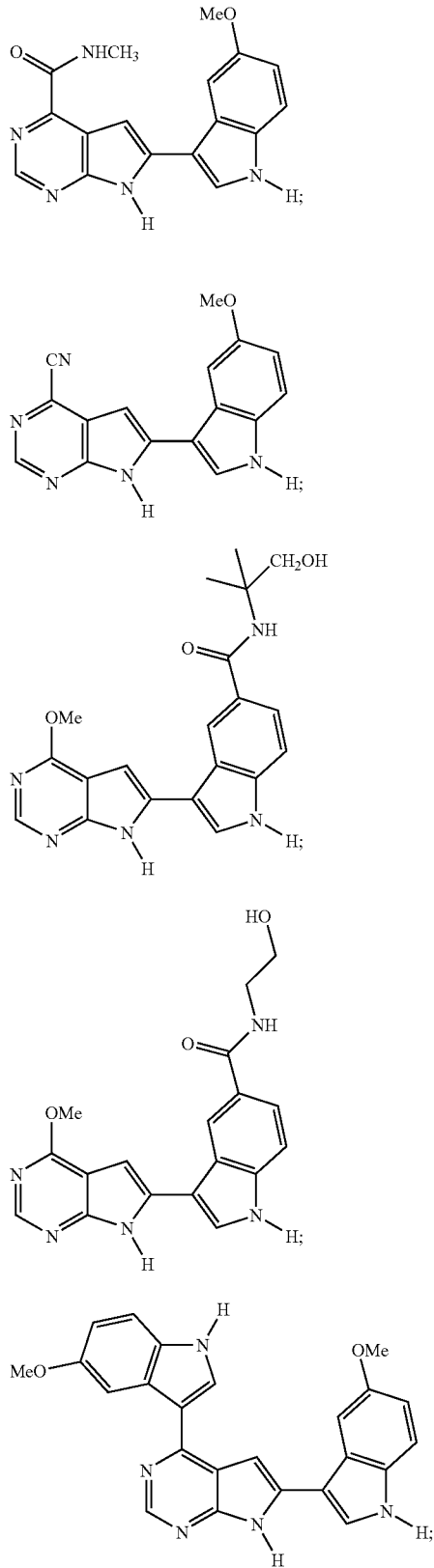

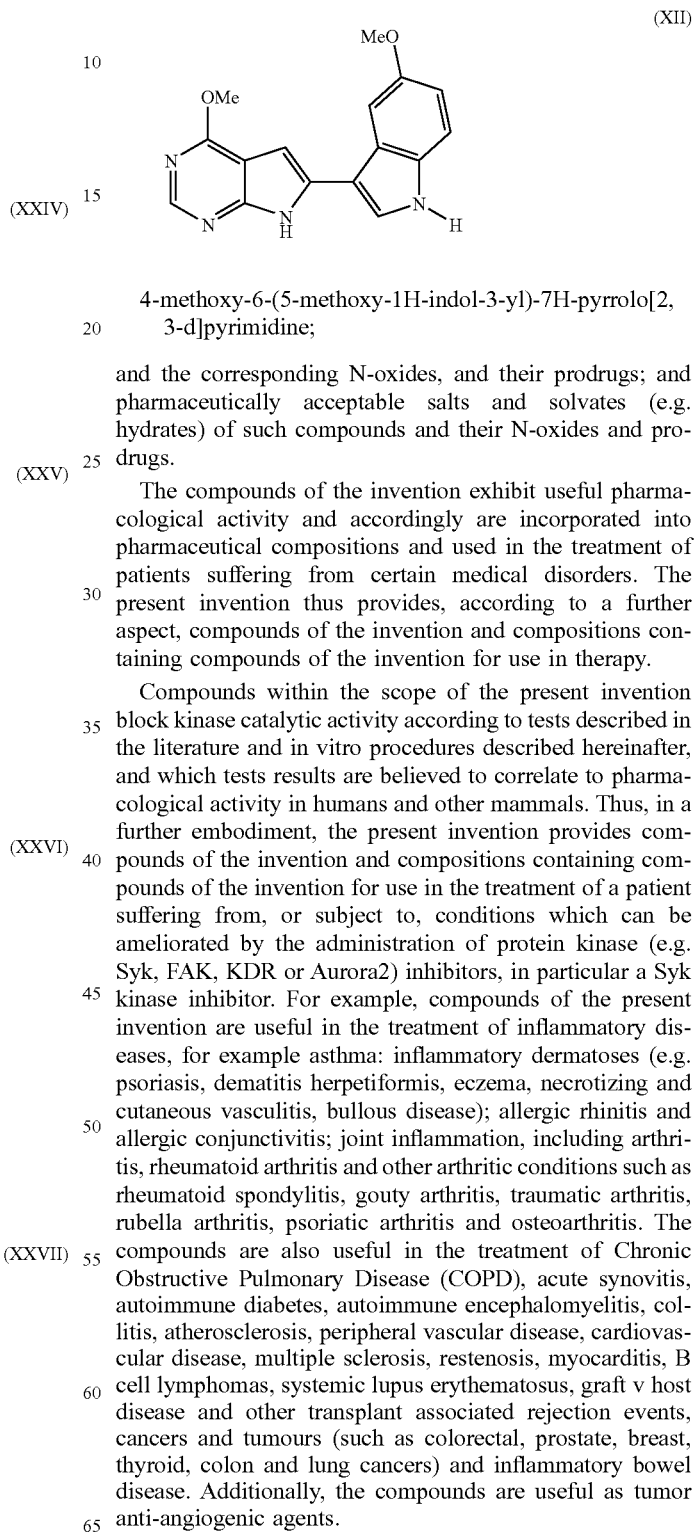

and the corresponding N-oxides, and their prodrugs; and pharmaceutically acceptable salts and solvates (e.g. hydrates) of such compounds and their N-oxides and prodrugs.

Especially preferred compounds of the invention are:

4-methoxy-6-(5-methoxy-1H-indol-3-yl)-7H-pyrrolo[2,3-d]pyrimidine;

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block kinase catalytic activity according to tests described in the literature and in vitro procedures described hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of protein kinase (e.g. Syk, FAK, KDR or Aurora2) inhibitors, in particular a Syk kinase inhibitor. For example, compounds of the present invention are useful in the treatment of inflammatory diseases, for example asthma; inflammatory dermatoses (e.g. psoriasis, dematitis herpetiformis, eczema, necrotizing and cutaneous vasculitis, bullous disease); allergic rhinitis and allergic conjunctivitis; joint inflammation, including arthritis, rheumatoid arthritis and other arthritic conditions such as rheumatoid spondylitis, gouty arthritis, traumatic arthritis, rubella arthritis, psoriatic arthritis and osteoarthritis. The compounds are also useful in the treatment of Chronic Obstructive Pulmonary Disease (COPD), acute synovitis, autoimmune diabetes, autoimmune encephalomyelitis, collitis, atherosclerosis, peripheral vascular disease, cardiovascular disease, multiple sclerosis, restenosis, myocarditis, B cell lymphomas, systemic lupus erythematosus, graft v host disease and other transplant associated rejection events, cancers and tumours (such as colorectal, prostate, breast, thyroid, colon and lung cancers) and inflammatory bowel disease. Additionally, the compounds are useful as tumor anti-angiogenic agents.

A special embodiment of the therapeutic methods of the present invention is the treating of asthma.

Another special embodiment of the therapeutic methods of the present invention is the treating of psoriasis.

Another special embodiment of the therapeutic methods of the present invention is the treating of joint inflammation.

Another special embodiment of the therapeutic methods of the present invention is the treating of inflammatory bowel disease.

Another special embodiment of the therapeutic methods of the present invention is the treating of cancers and tumours.

According to a further feature of the invention there is provided a method for the treatment of a human or animal patient suffering from, or subject to, conditions which can be ameliorated by the administration of a protein kinase (e.g. Syk, FAK, KDR or Aurora2) inhibitor for example conditions as hereinbefore described, which comprises the administration to the patient of an effective amount of a compound of the invention or a composition containing a compound of the invention. "Effective amount" is meant to describe an amount of compound of the present invention effective in inhibiting the catalytic activity a protein kinase, such as Syk, FAK, KDR or Aurora2, and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice, compounds of the present invention may be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient.

In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $R^2$ and $R^3$ are as hereinbefore defined, are prepared by reaction of compounds of formula (XXVIII):

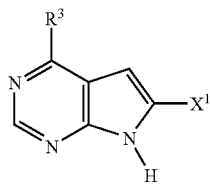

(XXVIII)

wherein $R^3$ is as hereinbefore defined and $X^1$ is a halogen, preferably iodine, atom or a triflate group, with compounds of formula (XXIX):

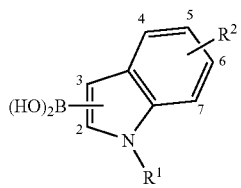

(XXIX)

wherein $R^1$ and $R^2$ are as defined hereinbefore. The coupling reaction may conveniently be carried out, for example, in the presence of a complex metal catalyst such as tetrakis(triphenylphosphine)palladium(0) and sodium bicarbonate, in aqueous dimethylformamide at a temperature up to reflux temperature. This reaction is conveniently carried out with the pyrrole NH in compound (XXVIII) protected with for example a tosyl group and the indole NH in compound (XXIX) protected with, for example, a tert-butyloxycarbonyl group.

Compounds of formula (I) wherein $R^2$ and $R^3$ are as hereinbefore defined and $R^1$ is optionally substituted alkyl are prepared by reaction of the corresponding compounds of formula (I) wherein $R^2$ and $R^3$ are as hereinbefore defined and $R^1$ is hydrogen with the appropriate alkyl halide $R^2$—$X^2$ in which $R^2$ is optionally substituted alkyl and $X^2$ is halo. This reaction is particularly suitable for the preparation of compounds of formula (I) wherein R1 is morpholinoacetyl.

Compounds of the invention may also be prepared by interconversion of other compounds of the invention.

Thus, for example, compounds of formula (I) containing a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) containing a carboxy group may be prepared by acid catalysed removal of the tert-butyl group of the corresponding tert-butyl esters using standard reaction conditions, for example reaction with trifluoroacetic acid at a temperature at about room temperature.

As another example compounds of formula (I) containing a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another example of the interconversion process, compounds of formula (I) containing a —C(=O)—$NY^1Y^2$ group may be prepared by coupling compounds of formula (I) containing a carboxy group with an amine of formula $HNY^1Y^2$ to give an amide bond using standard peptide coupling procedures, for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide) at room temperature. This procedure is particularly useful for the preparation of (i) compounds of formula (I) wherein $R^3$ represents —C(=O)—$NY^1Y^2$ or (ii) compounds of formula (1) wherein $R^2$ represents —C(=O)—$NY^1Y^2$. The coupling may also be brought about by reaction of compounds of formula (I) containing a carboxy group with N-{(dimethylamino)(1H-1,2,3-triazaolo[4,5-b]pyridin-1-yl)methylene}-N-methylmethanaminium hexafluorophosphate N-oxide in the presence of a suitable base, such as diisopropylethylamine, in an inert solvent, such as dimethylformamide, and at a temperature at about room temperature, followed by reaction with an amine of formula $HNY^1Y^2$ (ammonium chloride can be used for the preparation of compounds of formula (I) containing a —C(=O)—$NH_2$ group). The coupling may also be brought about by reaction of compounds of formula (I) containing a carboxy group with 2-(1H-benzotriazole-1-yl)1,1,3,3-tetramethyluronium hexafluorophosphate, in dry dimethylformamide, followed by reaction with an amine of formula $HNY^1Y^2$ in the presence of diisopropylethylamine. As another example of the interconversion process, compounds of formula (I) containing a —$CH_2OH$ group may be prepared by the reduction of corresponding compounds of formula (I) containing a —CHO or —$CO_2R^7$ (in which $R^7$ is lower alkyl) group. For example, the reduction may conveniently be carried out by means of reaction with lithium aluminium hydride, in an inert solvent, such as tetrahydrofuran, and at a temperature from about room temperature to about reflux temperature.

As another example of the interconversion process, compounds of formula (I) in which $R^2$ is hydroxy may be prepared by reaction of the corresponding compounds of formula (I) in which $R^1$ is methoxy with a Lewis acid, such as boron tribromide, in an inert solvent, such as dichloromethane and at a temperature from about 0° C. to about room temperature.

As another example of the interconversion process, compounds of formula (1) in which $R^2$ is —$OR^4$ (in which $R^4$ is optionally substituted alkyl, cycloalkyl, cycloalkylalkyl, heterocycloalkyl or heterocycloalkylalkyl) may be prepared by alkylation the corresponding compounds of formula (I) in which $R^2$ is hydroxy, with compounds of formula (XXX):

$R^4$—$X^3$ (XXX)

wherein $R^4$ is as just hereinbefore defined and $X^3$ is a halogen, preferably bromo, atom, or a tosyl group, using standard alkylation conditions. The alkylation may for example be carried out in the presence of a base, such as an alkali metal carbonate (e.g. potassium carbonate or cesium carbonate), an alkali metal alkoxide (e.g. potassium tertiary butoxide) or alkali metal hydride (e.g. sodium hydride), in dimethylformamide, or dimethyl sulfoxide, at a temperature from about 0° C. to about 100° C.

As another example of the interconversion process, compounds of formula (I) in which $R^1$ is alkyl, alkenyl, cycloalkyl, heterocycloalkyl, or alkyl substituted by —C(=O)NY$^1$Y$^2$, —OR$^7$, —C(=O)—OR$^7$, —NY$^1$Y$^2$ may be prepared by alkylation of the corresponding compounds of formula (Ia) in which $R^1$ is hydrogen, with the appropriate halide of formula (XXXI):

$$R^1\text{—}X^4 \qquad\qquad (XXXI)$$

wherein $R^1$ is alkyl, alkenyl, cycloalkyl, heterocycloalkyl, or alkyl substituted by —C(=O)NY$^1$Y$^2$, —OR$^7$, —C(=O)—OR$^7$, —NY$^1$Y$^2$ and $X^4$ is a halogen, preferably bromine, atom, using standard alkylation conditions for example those described hereinbefore.

As another example of the interconversion process, compounds of formula (I) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulfate in a medium such as aqueous methanol, buffered to about pH5, at temperatures between about 0° C. and room temperature. This latter method is preferred for compounds containing an acid-labile group.

As another example of the interconversion process, compounds of formula (I) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I) containing a cyano group may be prepared by reaction of the corresponding compounds of formula (I) containing a —C(=O)—NH$_2$ group with phosphorus pentachloride in the presence of triethylamine. The reaction may conveniently be carried out in an inert solvent, such as tetrahydrofuran, and at a temperature at about reflux temperature.

As another example of the interconversion process, compounds of formula (I) containing a —C(=O)—NH$_2$ group may be prepared by reaction of the corresponding compounds of formula (I) containing a cyano group with hydrogen peroxide in the presence of sodium hydroxide. The reaction may conveniently be carried out in methanol at a temperature at about room temperature.

As another example of the interconversion process, compounds of formula (I) in which $R^3$ is —NY$^1$Y$^2$ (wherein $Y^1$ and $Y^2$ are as hereinbefore defined), may be prepared by reaction of the corresponding compounds of formula (I) in which $R^3$ is halo (e.g. chloro) with an amine of formula HNY$^1$Y$^2$ (wherein $Y^1$ and $Y^2$ are as immediately hereinbefore defined).

As another example of the interconversion process, compounds of formula (I) in which $R^3$ is cyano may be prepared by reaction of compounds of formula (I) in which $X^1$ is halo, preferably chloro, with zinc cyanide in the presence of zinc powder, [1'1-bis(diphenylphosphino)ferrocene]dichloropalladium(II) complex and dichloromethane (catalytic amount) and N,N-dimethylacetamide at a temperature up to about 150° C.

As another example of the interconversion process, compounds of formula (1) containing a —C(=O)—OR$^5$ group (in which $R^5$ is as hereinbefore defined) may be prepared by reaction of the corresponding compounds of formula (1) containing a —C(=O)—OH group with alcohols of formula $R^5$—OH. For example when $R^5$ is tert-butyl the reaction may conveniently be carried out in the presence of 1-1'-carbonyldiimidazole and 1,8-diazabicyclo[5.4.0]undec-7-ene at a temperature at about room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Intermediates of formula (XXVIII) wherein $R^3$ is as hereinbefore defined, $X^1$ is iodo and the pyrrole NH is protected with a tosyl group may be prepared as shown in scheme 1.

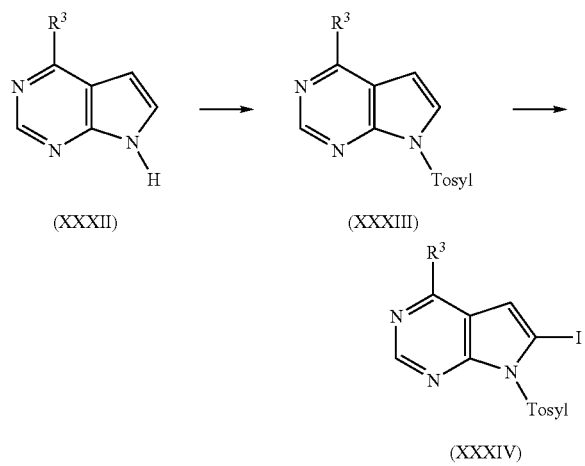

SCHEME 1

Thus for example compounds of formula (XXXIV) may be prepared by:
(i) reaction of compounds of formula (XXXII) with para-toluenesulfonyl chloride in the presence of aqueous sodium hydroxide and tetrabutyl ammonium sulfate in an inert solvent, such as toluene, and at room temperature;
(ii) subsequent treatment of the resulting compound of formula (XXXIII) with butyl lithium in tetrahydrofuran, at a temperature at about −78° C.;
(iii) reaction of the resulting anion with iodine.

Intermediates of formula (XXXIII) wherein $R^3$ is heteroaryl may be prepared by reaction of compounds of formula (XXXIII) wherein $R^3$ is halo, e.g. chloro, with a borane of formula $R^3BEt_2$ wherein $R^3$ is heteroaryl. The reaction may conveniently be carried out in the presence of tetrakis(triphenylphosphine)palladium(0) and potassium carbonate, in tetrahydrofuran at a temperature up to reflux temperature. This reaction is particularly suitable for the preparation of compounds of formula (XXXIII) wherein $R^3$ is pyridyl.

Intermediates of formula (XXXIII) wherein $R^3$ is heteroaryl may also be prepared by reaction of compounds of formula (XXXIII) wherein $R^3$ is halo, e.g. chloro, with heteroaryl-boronic acids of formula $R^3B(OH)_2$ in the presence of tetrakis(triphenylphosphine)palladium(0) and aqueous sodium bicarbonate, in dimethylformamide at a temperature up to reflux temperature. This reaction is particularly suitable for the preparation of compounds of formula (XXXIII) wherein $R^3$ is optionally substituted indolyl.

Intermediates of formula (XXXIII) wherein $R^3$ is $OR^4$, in which $R^4$ is as hereinbefore defined, may be prepared by reaction of compounds of formula (XXXIII) wherein $R^3$ is halo, e.g. chloro, with compounds of formula $R^4ONa$ (prepared by reacting alcohols of formula $R^4OH$ with sodium) at a temperature up to about 65° C. This reaction is particularly suitable for the preparation of compounds of formula (XXXIII) wherein $R^3$ is OMe.

The present invention is further exemplified but not limited by the following illustrative Examples and Reference Examples.

High Pressure Liquid Chromatography—Mass Spectrometry (LC-MS) conditions for determination of retention times ($R_T$) were as follows:

Method A: Hypersil BDS C-18 column (4.6 mm×50 mm) reverse phase operated under gradient elution conditions with mixtures of (A) water containing 0.05% trifluoroacetic acid and (B) acetonitrile containing 0.05% trifluoroacetic acid as the mobile phase gradient:(0.00 minutes 100% A:0% B; linear gradient to 100% B at 2 minutes; then hold until 3.5 minutes); flow rate 1 mL/minute with approximately 0.25 mL/minute split to the Mass Spectrometer; injection volume 10 µL; Hewlett Packard Model HP1100 Series UV detector wavelength 200 nm; Evaporative light scattering (ELS) detection—temperature 46° C., nitrogen pressure 4 bar.

Method B: Gilson 215 injector model using a Hypersil HyPURITY C-18-5µ column (4.6 mm×50 mm) operated under gradient elution conditions with mixtures of (A) water containing 0.05% trifluoroacetic acid and (B) acetonitrile containing 0.05% trifluoroacetic acid as the mobile phase gradient: (0.00 minutes 95% A:5% B; linear gradient to 95% B at 4 minutes; then to 5% B at 4.5 minutes, then hold until 6 minutes); injection volume 5 µL and flow rate 1 mL/minute to UV (DAD) detector followed by approximately 0.100 mL/minute split to the Mass Spectrometer (positive electrospray) with remainder to ELS detector.

METHOD C: Micromass instrument model LCT linked to an HP 1100 model instrument. Compound abundance were detected using an HP model G1315A photodiode array detector in the 200-600 nm wavelength range and a Sedex model 65 evaporative light scattering detector. Mass spectra were acquired in the 180 to 800 range. Data were analysed using the Micromass MassLynx software. Separation were carried out on a Hypersil BDS C18, 3 µm particle size column (50×4.6 mm) eluted by a linear gradient of 5 to 90% acetonitrile containing 0.05% (v/v) trifluoroacetic acid in water containing 0.05% (v/v) trifluoroacetic acid in 3.5 minutes at a flow rate of 1 ml/minute. The total runtime including column reequilibration was 7 minutes.

EXAMPLE 1

2-[5-Methoxy-3-(4-trifluoromethyl-7H-pyrrolo[2,3-b]pyrimidin-6-yl)-indol-1-yl]-1-morpholin-4-yl-ethanone The compound of formula (I), wherein $R^1$ is

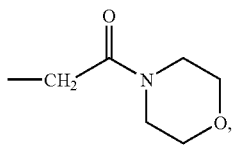

$R^2$ is —OMe, $R^3$ is —CF$_3$, the group

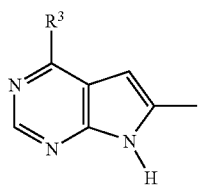

is attached to the 3 position of the indole ring and the group $R^2$ is attached to the 5 position of the indole ring, represented by formula (II):

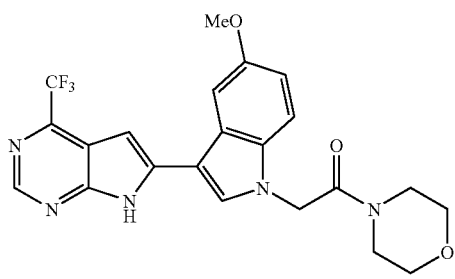

is prepared as shown in the following scheme:

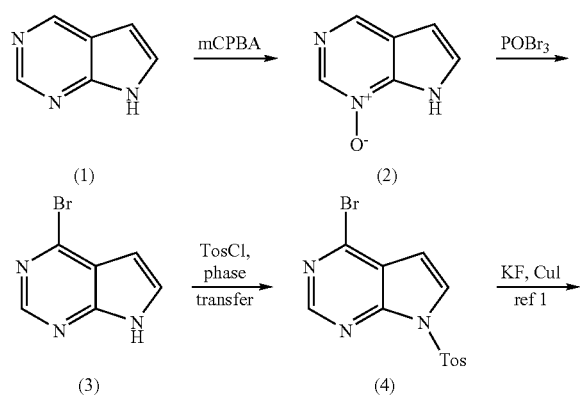

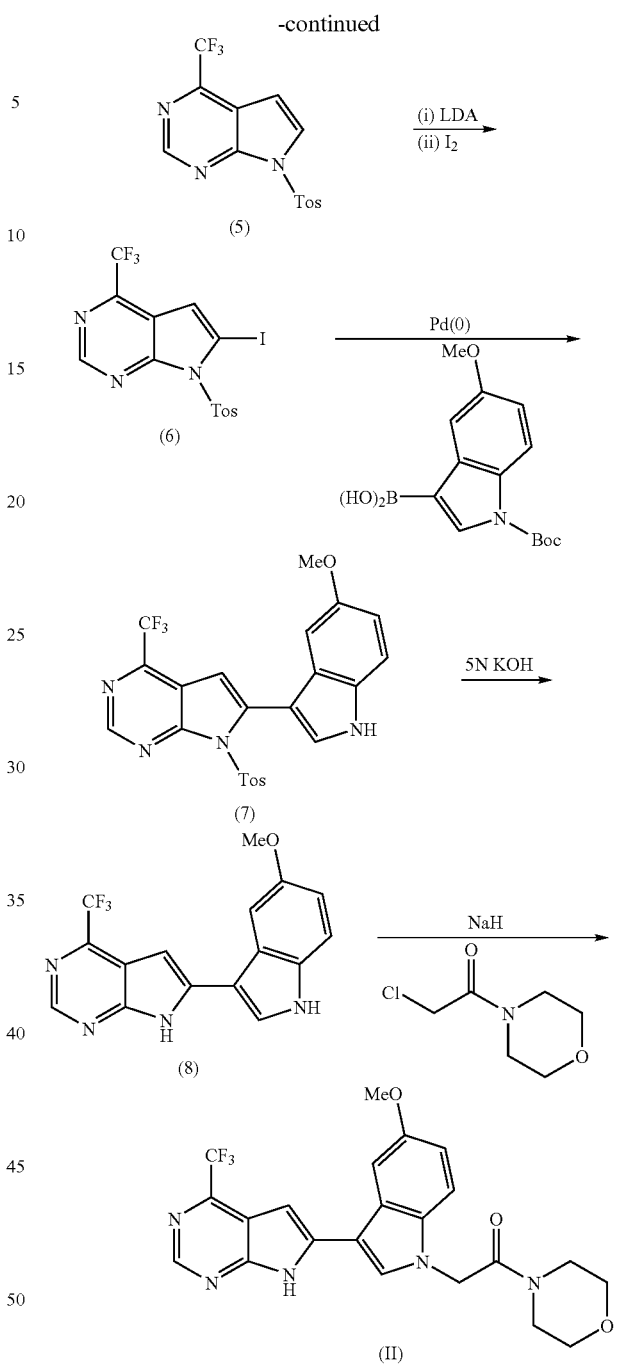

(i) treatment of 7H-pyrrolo[2,3-b]pyrimidine (1) with 3-chloroperbenzoic acid in dichloromethane at about 0° C. to give 7H-pyrrolo[2,3-b]pyrimidine-N-oxide (2);

(ii) reaction of (2) with phosphorous oxybromide at about 50° C. to give 4-bromo-7H-pyrrolo[2,3-b]pyrimidine (3);

(iii) reaction of (3) with 4-toluene sulfonyl chloride in the presence of tetrabutylammonium sulfate and aqueous sodium hydroxide in toluene, to give 4-bromo-7H-pyrrolo[2,3-b]pyrimidine (4);

(iv) reaction of (4) with trifluoromethyltrimethylsilane in the presence of potassium fluoride and copper(I) iodide in dimethylformamide at about 60° C., to give 7-(toluene-4-sulfonyl)-4-trifluoromethyl-7H-pyrrolo[2,3-b]pyrimidine (5);

(v) treatment of (5) with lithium diisopropylamide in tetrahydrofuran, at about −78° C., followed by reaction of the resulting anion with iodine to give 6-iodo-7-(toluene-4-sulfonyl)-4-trifluoromethyl-7H-pyrrolo[2,3-b]pyrimidine (6).

(vi) coupling of (6) with 1-tert-butyloxycarbonyl-5-methoxy-1H-indole-3-boronic acid in the presence of tetrakis(triphenylphosphine)palladium(0) and sodium bicarbonate, in aqueous dimethylformamide at about reflux temperature and removal of the tert-butyloxycarbonyl protecting group followed by treatment with methyl iodide in the presence of sodium hydride, in tetrahydrofuran, to give 6-(5-methoxy-1H-indol-3-yl)-7-(toluene-4-sulfonyl)-4-trifluoromethyl-7H-pyrrolo[2,3-b]pyrimidine (7);

(viii) removal of the tosyl protecting group in (7) by treatment with potassium hydroxide in methanol to give 6-(5-methoxy-1H-indol-3-yl)-4-trifluoromethyl-7H-pyrrolo[2,3-b]pyrimidine (8); and (ix) alkylation of (8) with 4-(2-chloroacetyl)morpholine in the presence of sodium hydride, in dimethylformamide to give 2-[5-methoxy-3-(4-trifluoromethyl-7H-pyrrolo[2,3-b]pyrimidin-6-yl)-indol-1-yl]-1-morpholin-4-yl-ethanone (II).

EXAMPLE 2

1-Methyl-3-(7H-pyrrolo[2,3-b]pyrimidine-6-yl)-1H-indole-5-carboxylic acid (2-hydroxy-1,1-dimethyl-ethyl)-amide The compound of formula (I), wherein R$^1$ is —CH$_3$, R$^2$ is

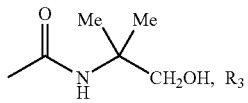

is —H, the group

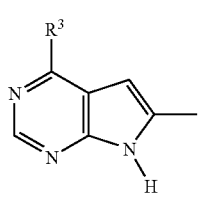

is attached to the 3 position of the indole ring and the group R$^2$ is attached to the 5 position of the indole ring, represented by formula (III):

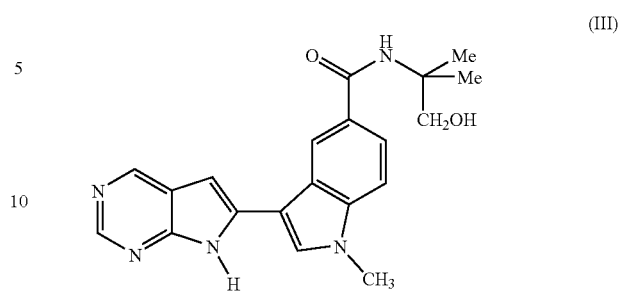

is prepared as shown in the following scheme:

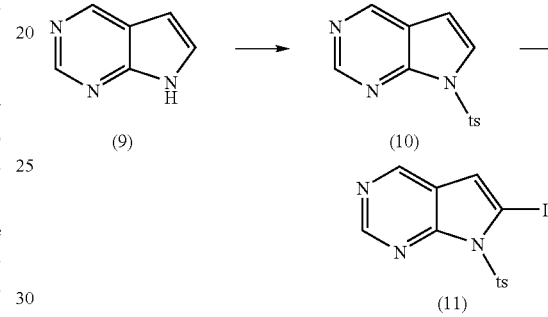

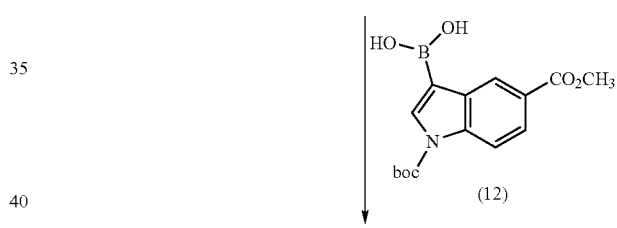

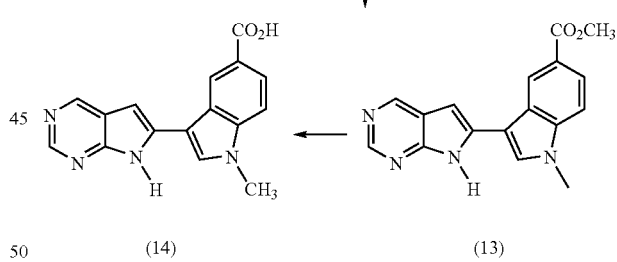

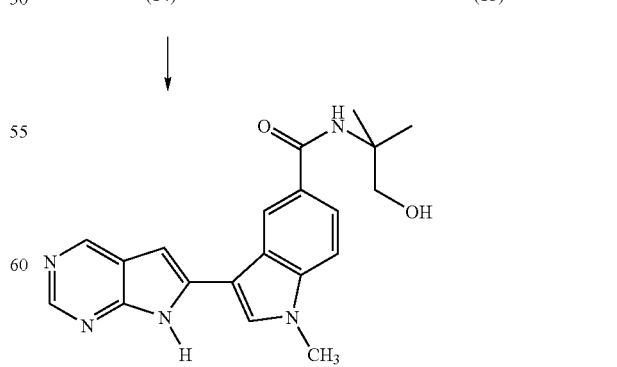

(i) reaction of (9) with 4-toluene sulfonyl chloride in the presence of tetrabutylammonium sulfate and aqueous sodium hydroxide in toluene, to give (10);
(ii) treatment of (10) with lithium diisopropylamide in tetrahydrofuran, at about −78° C., followed by reaction of the resulting anion with iodine to give (11);
(iii) coupling of (11) with 1-tert-butyloxycarbonyl-5-methoxy-1H-indole-3-boronic acid (12) in the presence of tetrakis(triphenylphosphine)palladium(0) and sodium bicarbonate, in aqueous dimethylformamide at about reflux temperature and removal of the tert-butyloxycarbonyl protecting group followed by treatment with methyl iodide in the presence of sodium hydride, in tetrahydrofuran, to give 6-[(1-methyl-5-carbomethoxyindole)$_3$-yl]-7H-pyrrolo[2,3-b]pyrimidine (13);
(iv) treatment of (13) with aqueous methanolic potassium hydroxide at reflux to give 6-[(1-methyl-5-carboxyindole)$_3$-yl]-7H-pyrrolo[2,3-b]pyrimidine (14); and
(v) coupling of (14) with 2-hydroxy-1,1-dimethylethylamine in the presence of O-(7-azabenzotriazol-1-yl)-1,1,3,3-tetramethyluronium hexafluorophosphate and diisopropylethylamine in dimethylformamide to give 1-methyl-3-(7H-pyrrolo[2,3-b]pyrimidine-6-yl)-1H-indole-5-carboxylic acid (2-hydroxy-1,1-dimethylethyl)-amide (III).

EXAMPLE 3

2-{[5-Methoxy-3-(7H-pyrrolo[2,3-b]pyrimidine-6-yl)-indol-1-yl]-1-morpholin-4-yl}-ethanone The compound of formula (1), wherein $R^1$ is

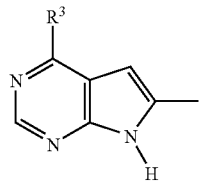

$R^2$ is —OMe, $R^3$ is —H, the group is attached to the 3 position of the indole ring and the group $R^2$ is attached to the 5 position of the indole ring, represented by formula (IV):

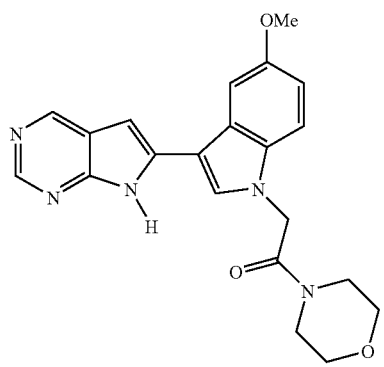

(IV)

is prepared as shown in the following scheme:

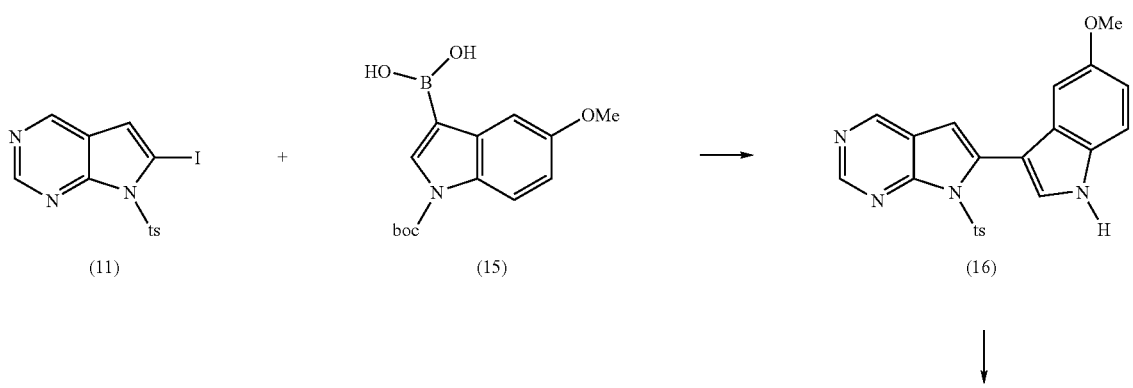

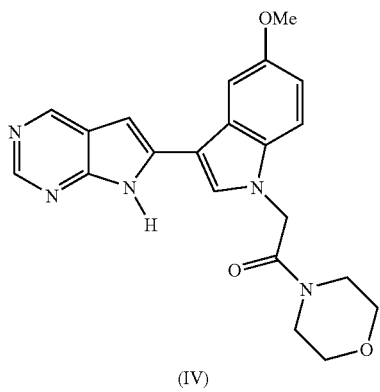

(IV)

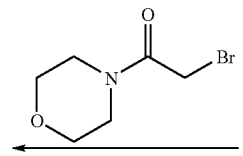

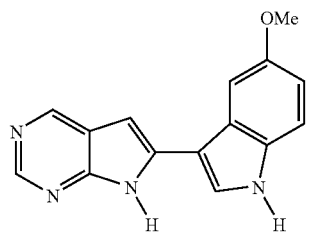

(17)

(i) coupling of 6-iodo-7-(toluene-4-sulfonyl)-7H-pyrrolo[2,3-b]pyrimidine (11) 1-tert-butyloxycarbonyl-5-methoxyindole-3-boronic acid (15) in the presence of tetrakis(triphenylphosphine)palladium(0) and sodium bicarbonate, in aqueous dimethylformamide at about reflux temperature and removal of the tert-butyloxycarbonyl protecting group, to give 6-[(5-methoxyindole)-3-yl]-7-(toluene-4-sulfonyl)-7H-pyrrolo[2,3-b]pyrimidine (16);

(ii) treatment of (16) with aqueous methanolic potassium hydroxide at reflux to give 6-[(5-methoxyindole)$_3$-yl]-7H-pyrrolo[2,3-b]pyrimidine (17); and (iii) reaction of (17) with sodium hydride in dimethylformamide followed by reaction with 2-bromoacetic acid morpholineamide to give 2-{[5-methoxy-3-(7H-pyrrolo[2,3-b]pyrimidine-6-yl)-indol-1-yl]-1-morpholin-4-yl}-ethanone (IV).

EXAMPLE 4

The compound of formula (I), wherein $R^1$ is —CH$_2$CF$_3$, $R^2$ is —OMe, $R^3$ is —CN, the group

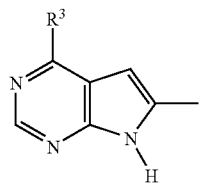

is attached to the 3 position of the indole ring and the group $R^2$ is attached to the 5 position of the indole ring, represented by formula (VII):

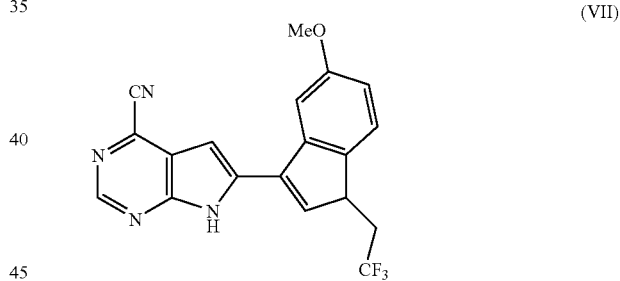

(VII)

is prepared as shown in the following scheme:

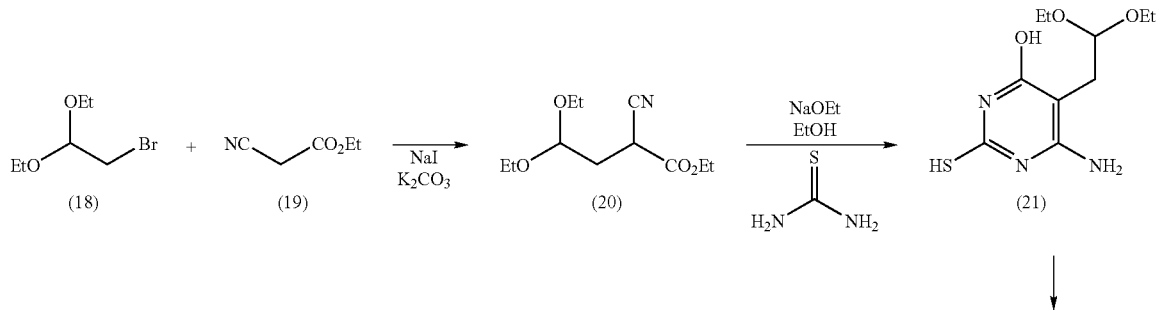

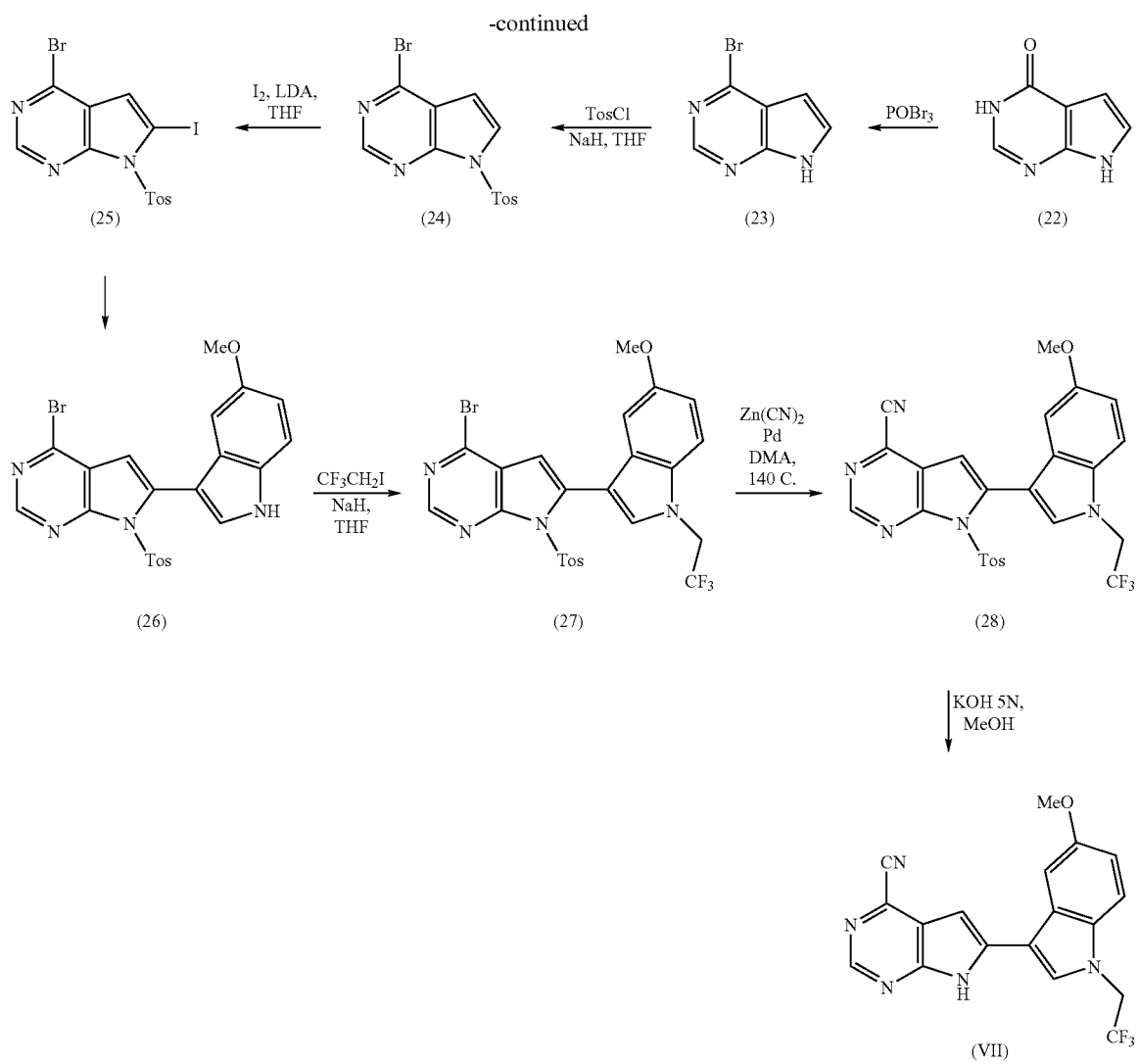

(i) reaction of (18) and (19) in the presence of potassium carbonate and sodium iodide to give (20);
(ii) reaction of (20) with thiourea in the presence of sodium ethoxide in ethanol to give (21);
(iii) cyclisation of (21) by heating in toluene at about reflux to give (22);
(iv) reaction of (22) with phosphorus oxybromide to give 4-bromo-7H-pyrrolo[2,3-b]pyrimidine (23);
(v) reaction of (23) with 4-toluenesulfonyl chloride in the presence of tetrabutylammonium sulfate and aqueous sodium hydroxide in toluene to give (24);
(vi) treatment of (24) with lithium diisopropylamide in tetrahydrofuran, at about −78° C., followed by reaction of the resulting anion with iodine to give (25);
(vii) coupling of (25) with 1-tert-butyloxycarbonyl-5-methoxyindole-3-boronic acid in the presence of tetrakis(triphenylphosphine)palladium(0) and sodium bicarbonate, in aqueous dimethylformamide at about reflux temperature and removal of the tert-butyloxycarbonyl protecting group, to give 4-bromo-6-[(5-methoxyindole)$_3$-yl]-7-(toluene-4-sulfonyl)-7H-pyrrolo[2,3-b]pyrimidine (26);
(viii) reaction of (26) with sodium hydride in tetrahydrofuran followed by reaction with 2-trifluoro-iodoethane to give (27);
(ix) reaction of (27) with zinc cyanide in the presence of palladium in N'N-dimethylaniline at about 140° C. to give (28); and
(x) treatment of (28) with aqueous methanolic potassium hydroxide at reflux to give (VII).

EXAMPLE 5

The compound of formula (I), wherein $R^1$ is —CH$_3$, $R^2$ is —OMe, $R^3$ is

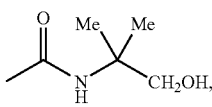

the group

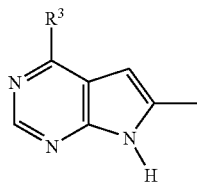

is attached to the 3 position of the indole ring and the group $R^2$ is attached to the 5 position of the indole ring, represented by formula (IX):

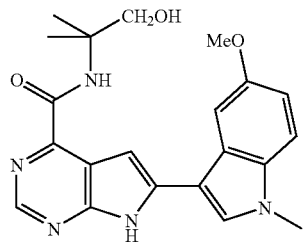

(IX)

is prepared as shown in the following scheme:

(ii) reaction of (26) with sodium hydride in tetrahydrofuran followed by reaction with methyl iodide to give (29);

(ii) reaction of (29) with carbon monoxide in the presence of palladium in methanol at reflux to give (30);

(iii) treatment of (30) with aqueous methanolic potassium hydroxide at reflux to give (31); and (iv) coupling of (31) with 2-hydroxy-1,1-dimethylethylamine in the presence of O-(7-azabenzotriazol-1-yl)-1,1,3,3-tetramethyluronium hexafluorophosphate and diisopropylethylamine in dimethylformamide to give (IX).

EXAMPLE 6

The compound of formula (1), wherein $R^1$ is

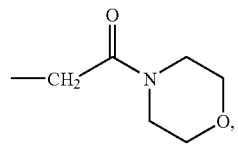

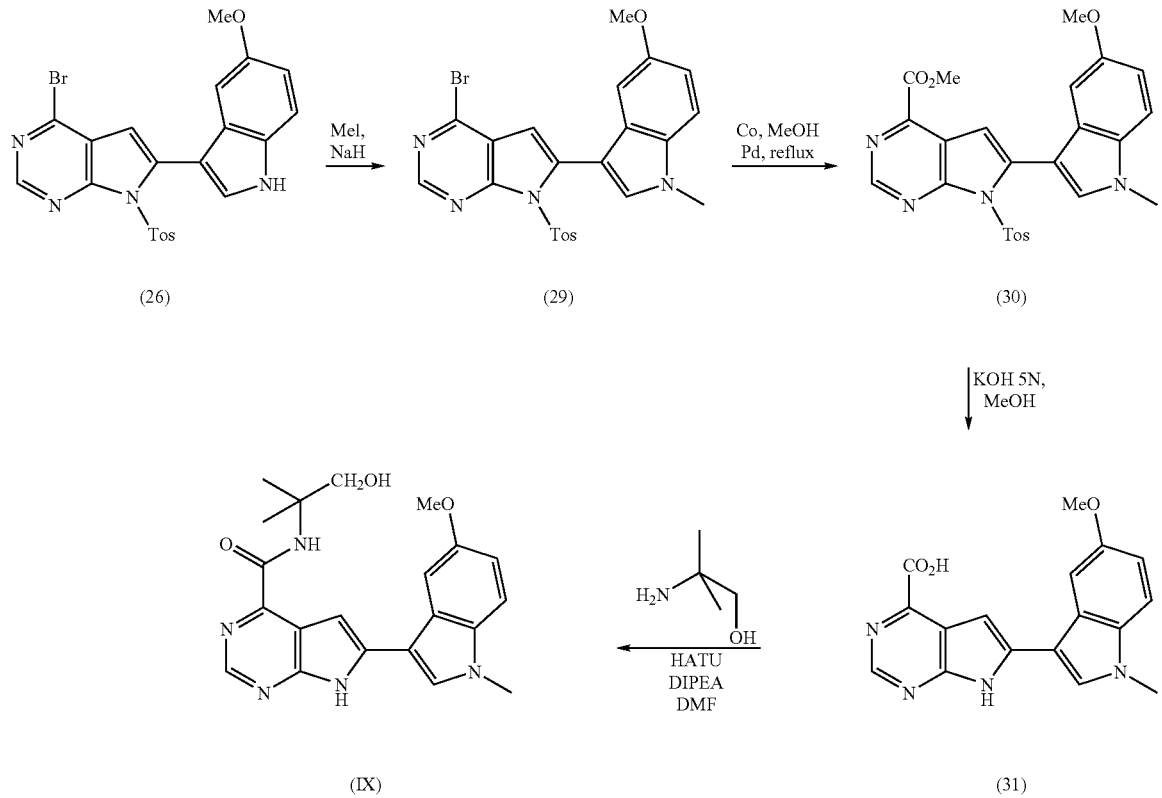

$R^2$ is —OMe, $R^3$ is
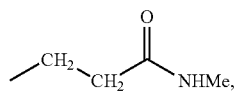
the group
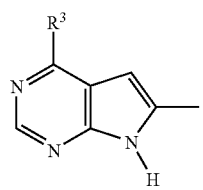
is attached to the 3 position of the indole ring and the group $R^2$ is attached to the 5 position of the indole ring, represented by formula (V):
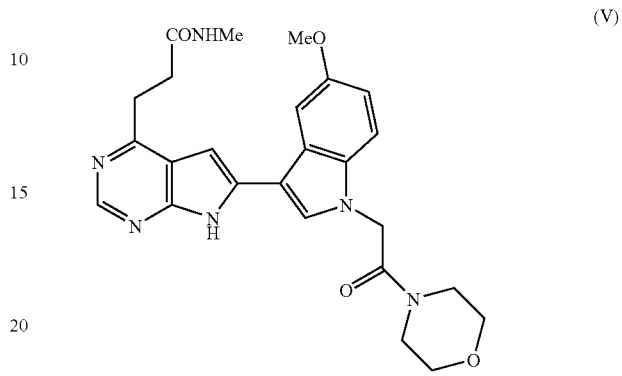
is prepared as shown in the following scheme:
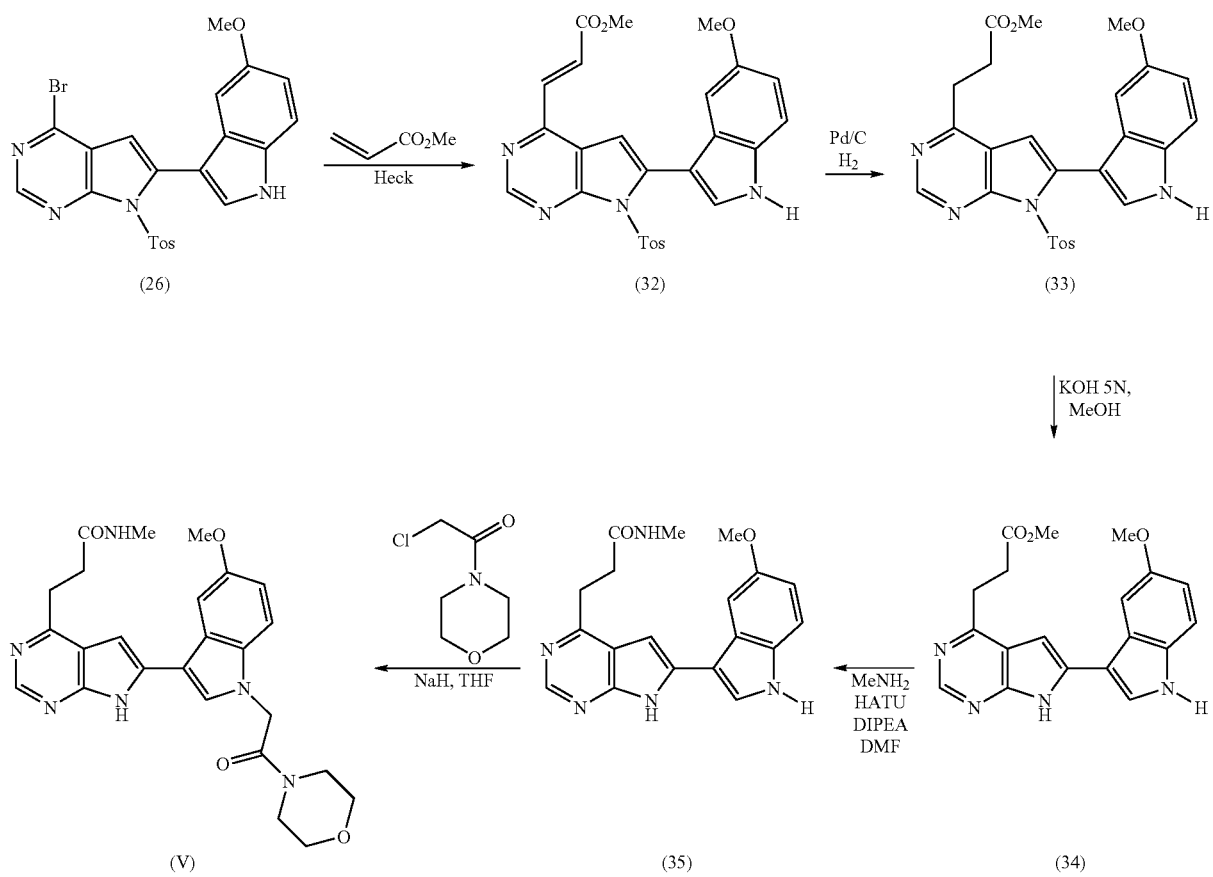

(i) reaction of (26) with methyl acrylate in the presence of palladium acetate, triphenyl phosphine and triethylamine at about 110° C. to give (32);
(ii) hydrogenation of (32) in the presence of palladium on carbon to give (33);
(iii) treatment of (33) with aqueous methanolic potassium hydroxide at reflux to give the acid (34);
(iv) coupling of (34) with methylamine in the presence of O-(7-azabenzotriazol-1-yl)-1,1,3,3-tetramethyluronium hexafluorophosphate and diisopropylethylamine in dimethylformamide to give (35); and
(v) alkylation of (35) with 4-(2-chloroacetyl)morpholine in the presence of sodium hydride, in dimethylformamide to give (V).

EXAMPLE 7

The compound of formula (I), wherein $R^1$ is

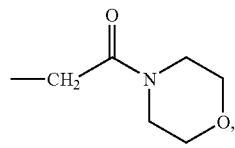

$R^2$ is —OMe, $R^3$ is

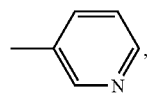

the group

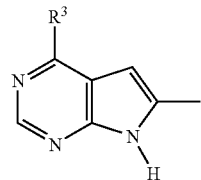

is attached to the 3 position of the indole ring and the group $R^2$ is attached to the 5 position of the indole ring, represented by formula (VI):

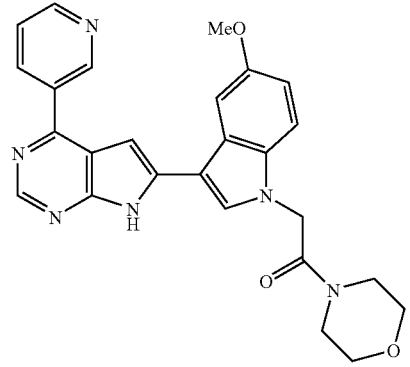

(VI)

is prepared as shown in the following scheme:

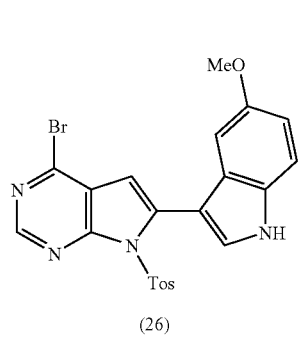

(26)

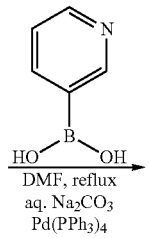

HO—B—OH
DMF, reflux
aq. Na₂CO₃
Pd(PPh₃)₄

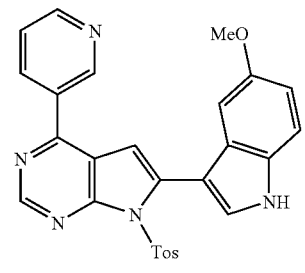

(36)

KOH 5N, MeOH

-continued

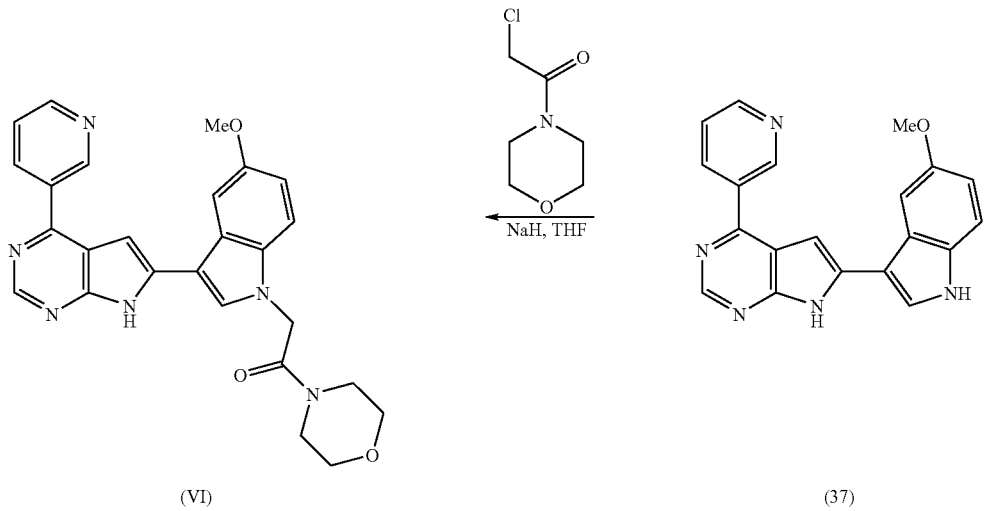

(VI)                                  (37)

(i) coupling of (26) with pyridine-3-boronic acid in the presence of tetrakis(triphenylphosphine)palladium(0) and sodium bicarbonate, in aqueous dimethylformamide at about reflux temperature to give 4-(pyridin-3-yl)-6-[(5-methoxyindole)3-yl]-7-(toluene-4-sulfonyl)-7H-pyrrolo[2,3-b]pyrimidine (36);
(ii) treatment of (36) with aqueous methanolic potassium hydroxide at reflux to give (37, Example 9); and
(iii) alkylation of (37, Example 9) with 4-(2-chloroacetyl) morpholine in the presence of sodium hydride, in dimethylformamide to give 2-[5-methoxy-3-(4-(pyridin-3-yl)-7H-pyrrolo[2,3-b]pyrimidin-6-yl)-indol-1-yl]-1-morpholin-4-yl-ethanone (VI).

EXAMPLE 8

The compound of formula (I), wherein $R^1$ is —CH$_2$CH$_3$, $R^2$ is —OMe, $R^3$ is

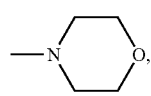

the group

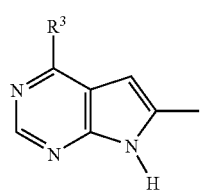

is attached to the 3 position of the indole ring and the group $R^2$ is attached to the 5 position of the indole ring, represented by formula (VIII):

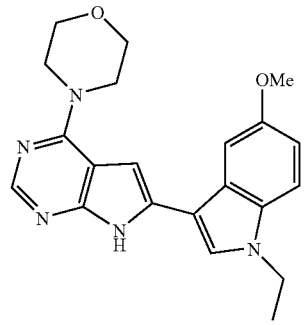

(VIII)

is prepared as shown in the following scheme:

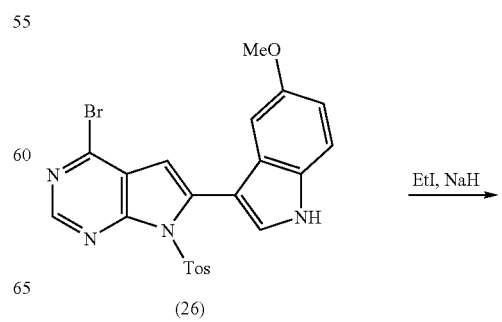

(26)

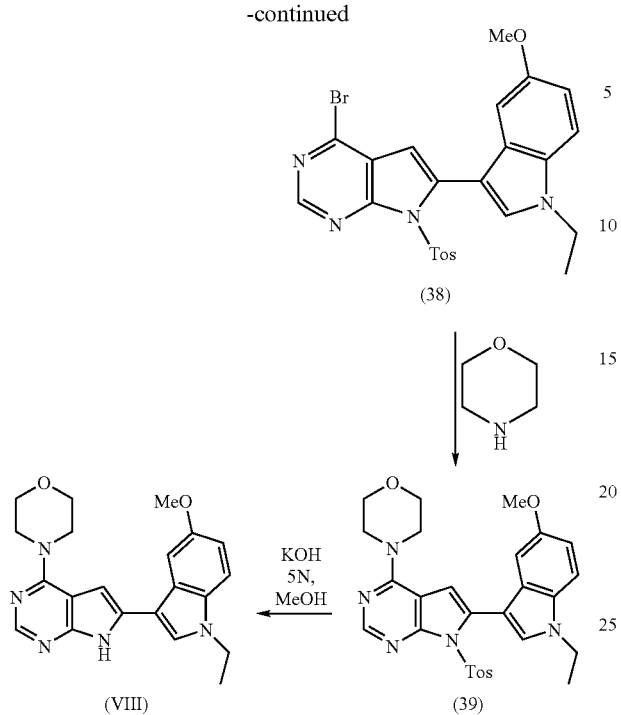

(i) alkylation of (26) with ethyl iodide in the presence of sodium hydride, in dimethylformamide to give (38);
(ii) reaction of (38) with morpholine in a microwave oven at about 200° C. in α,α,α-trifluorotoluene to give (39); and
(iii) treatment of (39) with aqueous methanolic potassium hydroxide at reflux to give (VIII).

EXAMPLE 9

6-(5-Methoxy-1H-indol-3-yl)-4-pyridin-3-yl-7H-pyrrolo[2,3-d]pyrimidine

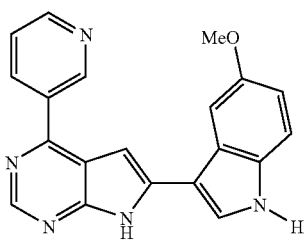

A solution of 6-iodo-7-[(4-methylphenyl)sulfonyl]-4-pyridin-3-yl-7H-pyrrolo[2,3-d]pyrimidine [260 mg, Reference Example 1] and 1-tert-butyl-carboxyl-5-methoxy-1H-indole-3-boronic acid [178 mg, Reference Example 12] in dimethylformamide (10 mL) was treated with palladium tetrakis triphenyl phosphine (13 mg) and sodium hydrogen carbonate (8 mg). The reaction mixture was stirred at reflux for 2 hours and allowed to cool to room temperature. The solution was evaporated under reduced pressure and the residue partitioned between water and ethyl acetate. The organic phase was separated, then dried over magnesium sulfate and then evaporated under reduced pressure. The residue was subjected to flash column chromatography on silica eluting with a mixture of ethyl acetate and methanol (95:5, v/v) to give 6-(5-Methoxy-1H-indol-3-yl)-4-pyridin-3-yl-7H-pyrrolo[2,3-d]pyrimidine (20 mg) as an amorphous solid. MS: 342 [MH]$^+$, LCMS (Method A) R$_T$=2.57 minutes.

EXAMPLE 10

4-Methoxy-6-(5-methoxy-1-methyl-1H-indol-3-yl)-7H-pyrrolo[2,3-d]pyrimidine

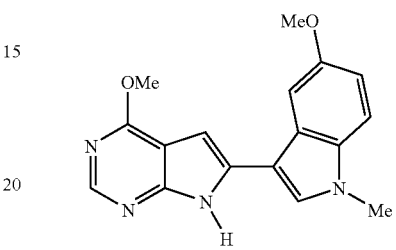

A solution of 4-methoxy-6-(5-methoxy-1-methyl-1H-indol-3-yl)-7-[(4-methylphenyl)sulfonyl]-7H-pyrrolo[2,3-d]pyrimidine [361 mg, Reference Example 4] in methanol (20 mL) was treated with potassium hydroxide (1.53 g). The reaction mixture was stirred for 16 hours at room temperature and refluxed 1 hour. The solution was evaporated under reduced pressure and the residue partitioned between water and ethyl acetate. The organic phase was separated, then dried over magnesium sulfate and evaporated under reduced pressure. The residue was triturated with diethyl ether to give 4-methoxy-6-(5-methoxy-1-methyl-1H-indol-3-yl)-7H-pyrrolo[2,3-d]pyrimidine (155 mg) as a solid m.p.=184° C. MS: 309 [MH]$^+$.

EXAMPLE 11

4-Methoxy-6-(5-methoxy-1H-indol-3-yl)-7H-pyrrolo[2,3-d]pyrimidine

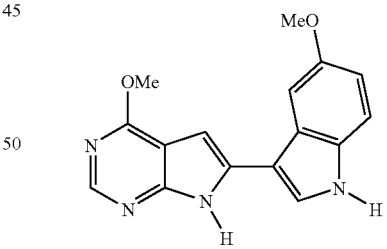

A solution of 4-methoxy-6-(5-methoxy-1H-indol-3-yl)-7-[(4-methylphenyl)sulfonyl]-7H-pyrrolo[2,3-d]pyrimidine [448 mg, Reference Example 5] in methanol (15 mL) was treated with potassium hydroxide (1.96 g). The reaction mixture was stirred for 2 hours at room temperature and the solvent was evaporated under reduced pressure. The residue was partitioned between water and ethyl acetate. The organic phase was separated, then dried over magnesium sulfate and then evaporated under reduced pressure. The residue was subjected to flash column chromatography on silica eluting with a mixture of ethyl acetate and cyclohexane (80:20, v/v) to give 4-methoxy-6-(5-methoxy-1H-indol- 3-yl)-7H-pyrrolo[2,3-d]pyrimidine (320 mg) as a yellow solid m.p. >260° C. MS: 295 [MH]+.

EXAMPLE 12

4-(5-Methoxy-1H-indol-3-yl)-6-(5-methoxy-1-methyl-1H-indol-3-yl)-7H-pyrrolo[2,3-d]pyrimidine

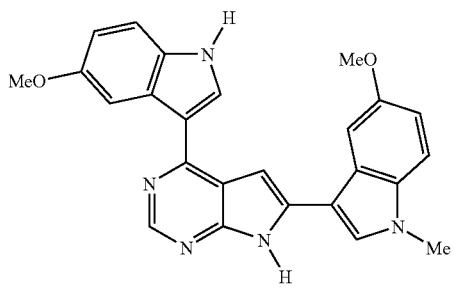

A solution of 4-(5-methoxy-1-[(4-methylphenyl)sulfonyl]-1H-indol-3-yl)-6-(5-methoxy-1H-indol-3-yl)-7-[(4-methylphenyl)sulfonyl]-7H-pyrrolo[2,3-d]pyrimidine [93 mg, Reference Example 9] in methanol (5 mL) was treated with potassium hydroxide (249 mg). The reaction mixture was stirred for 16 hours at room temperature. The solution was evaporated under reduced pressure and the residue partitioned between ethyl acetate and water. The organic phase was separated, then dried over magnesium sulfate and then evaporated under reduced pressure. The residue was purified by HPLC to give 4-(5-methoxy-1H-indol-3-yl)-6-(5-methoxy-1-methyl-1H-indol-3-yl)-7H-pyrrolo[2,3-d]pyrimidine (9 mg) as a gum. MS: 424 [MH]+. LCMS (Method B) $R_T$=3.15 minutes.

REFERENCE EXAMPLE 1

6-Iodo-7-[(4-methylphenyl)sulfonyl]-4-pyridin-3-yl-7H-pyrrolo[2,3-d]pyrimidine

To a solution of 7-[(4-methylphenyl)sulfonyl]4-pyridin-3-yl-7H-pyrrolo[2,3-d]pyrimidine [1 g, Reference Example 2] in tetrahydrofuran (20 mL) at −78° C. was added dropwise a solution of butyl lithium in hexane (2 mL, 1.6M) under inert atmosphere. The solution was stirred at that temperature for 1.5 hour and iodine (796 mg) was added. The reaction mixture was stirred at −78° C. for another 1 hour and allowed to reach room temperature. The reaction mixture was partitioned between ethyl acetate and aqueous sodium sulfite solution. The organic phase was separated, then dried over magnesium sulfate and then evaporated under reduced pressure. The residue was subjected to flash column chromatography on silica eluting with a gradient of ethyl acetate and cyclohexane (50:50, to 100, v/v) to give the title compound (260 mg) as an amorphous solid. MS: 477 [MH]+. LCMS (Method B) $R_T$=3.26 minutes.

REFERENCE EXAMPLE 2

7-[(4-Methylphenyl)sulfonyl]-4-pyridin-3-yl-7H-pyrrolo[2,3-d]pyrimidine

A solution of 4-chloro-7-[(4-methylphenyl)sulfonyl]-7H-pyrrolo[2,3-d]pyrimidine [4 g, Reference Example 3] and diethyl-3-pyridyl-borane (2.1 g) in tetrahydrofuran (180 mL) was treated with palladium tetrakis triphenylphosphine (0.65 g) and potassium carbonate (3.59 g). The solution was stirred at reflux for 24 hours and evaporated under reduced pressure. The residue was partitioned between ethyl acetate and brine. The organic phase was separated, then dried over magnesium sulfate and then evaporated under reduced pressure. The residue was subjected twice to flash column chromatography on silica eluting with a mixture of ethyl acetate and methanol (90:10, v/v) and a mixture of ethyl acetate and cyclohexane (50:50, v/v) to give the title compound (2.5 g) as an amorphous solid. MS: 351 [MH]+. LCMS (Method B) $R_T$=3.05 minutes.

REFERENCE EXAMPLE 3

4-Chloro-7-[(4-methylphenyl)sulfonyl]-7H-pyrrolo[2,3-d]pyrimidine

A solution of 4-chloro-7H-pyrrolo[2,3-d]pyrimidine (Reference: Gerster, John F.; Hinshaw, Barbara C.; Robins, Roland K.; Townsend, Leroy B. Study of electrophylic substitution in the pyrrolo[2,3-d]pyrimidine ring. J. Heterocycl. Chem. (1969), -(2), 207-213) (20 g) and para-toluene sulfonylchloride (28.6 g) in toluene (1L) was treated with a solution of sodium hydroxide (50 g) in water (800 mL), and tetrabutyl ammonium sulfate (462 mg). The solution was stirred vigorously at room temperature for 2 hours and partitioned between ethyl acetate and brine. The organic phase was separated, then dried over magnesium sulfate and then evaporated under reduced pressure. The residue was subjected to flash column chromatography on silica eluting with a gradient of ethyl acetate and cyclohexane (50:50 to 80:20, v/v) to give the title compound (2.5 g) as a solid m.p.=143° C. LCMS (Method B) $R_T$=2.78 minutes.

REFERENCE EXAMPLE 4

4-Methoxy-6-(5-methoxy-1-methyl-1H-indol-3-yl)-7-[(4-methylphenyl)sulfonyl]-7H-pyrrolo[2,3-d]pyrimidine To a solution of 4-methoxy-6-(5-methoxy-1H-indol-3-yl)-7-[(4-methylphenyl)sulfonyl]-7H-pyrrolo[2,3-d]pyrimidine [448 mg, Reference Example 5] in dimethylformamide (20 mL) was added the sodium hydride (44 mg, 60% dispersion in oil) and methyl iodide (156 mg) under inert atmosphere. The solution was stirred for 1 hour at room temperature and the solvent was evaporated under reduced pressure. The residue was partitioned between water and ethyl acetate. The organic phase was separated, then dried over magnesium sulfate and then evaporated under reduced pressure. The residue was subjected to flash column chromatography on silica eluting with a mixture of ethyl acetate and cyclohexane (30:70, v/v) to give the title compound (260 mg) as an amorphous solid. MS: 464 [MH]+. LCMS (Method B) $R_T$=4.39 minutes.

REFERENCE EXAMPLE 5

4-Methoxy-6-(5-methoxy-1H-indol-3-yl)-7-[(4-methylphenyl)sulfonyl]-7H-pyrrolo-[2,3-d]pyrimidine A solution of 6-iodo-4-methoxy-7-[(4-methylphenyl)sulfonyl]-7H-pyrrolo[2,3-d]pyrimidine [1.98 g, Reference Example 6] and 1-tert-butyl-carboxyl-5-methoxy-1H-indole-3-boronic acid [1.26 g, Reference Example 12] in dimethylformamide (40 mL) was treated successively with a saturated aqueous solution of sodium bicarbonate (10 mL) and palladium tetrakis triphenylphosphine (165 mg). The reaction mixture was stirred at reflux for 3 hours and the solvent was evaporated under reduced pressure. The residue was partitioned between ethyl acetate and water. The organic phase was separated, then dried over magnesium sulfate and then evaporated under reduced pressure. The residue was subjected to flash column chromatography on silica eluting with a mixture of ethyl acetate and cyclohexane (50:50, v/v) to give the title compound (1.8 g) as a grey solid. m.p.=131° C. MS: 450 [MH]$^+$.

REFERENCE EXAMPLE 6

6-Iodo-4-methoxy-7-[(4-methylphenyl)sulfonyl]-7H-pyrrolo[2,3-d]pyrimidine

To a solution of 4-methoxy-7-[(4-methylphenyl)sulfonyl]-7H-pyrrolo[2,3-d]pyrimidine [2.23 g, Reference Example 7] in tetrahydrofuran (35 mL) at −78° C. was added drop wise a solution of butyl lithium in hexane (5 mL, 1.6M) under inert atmosphere. The solution was stirred at −70° C. for 1 hour and iodine (2.05 g) was added. The reaction mixture was stirred at −70° C. for another 1 hour, allowed to reach room temperature and partitioned between ethyl acetate and aqueous sodium sulfite solution. The organic phase was separated, then dried over magnesium sulfate and then evaporated under reduced pressure to give the title compound (2.64 g) as an amorphous solid. MS: 430 [MH]$^+$. LCMS (Method B) $R_T$=4.15 minutes.

REFERENCE EXAMPLE 7

4-Methoxy-7-[(4-methylphenyl)sulfonyl]-7H-pyrrolo[2,3-d]pyrimidine

A solution of 4-methoxy-7H-pyrrolo[2,3-d]pyrimidine [1.2 g, Reference Example 8] and para-toluene sulfonyl-chloride (1.77 g) in toluene (60 mL) was treated with a solution of sodium hydroxide (3.2 g) in water (30 mL), and tetrabutyl ammonium sulfate (27 mg). The solution was stirred vigorously at room temperature for 4 hours and partitioned between ethyl acetate and brine. The organic phase was separated, then dried over magnesium sulfate and then evaporated under reduced pressure. The residue was subjected to flash column chromatography on silica eluting with a gradient of ethyl acetate and cyclohexane (50:50 to 80:20, v/v) to give the title compound (2.23 g) as an amorphous solid. MS: 304 [MH]$^+$. LCMS (Method B) $R_T$=3.88 minutes.

REFERENCE EXAMPLE 8

4-Methoxy-7H-pyrrolo[-2,3-d]pyrimidine

To a solution of sodium methoxide prepared by adding portion wise the sodium (2 g) in methanol (100 mL) under an inert atmosphere, was added 4-chloro-7H-pyrrolo[2,3-d]pyrimidine (Reference: Gerster, John F.; Hinshaw, Barbara C.; Robins, Roland K.; Townsend, Leroy B. Study of electrophylic substitution in the pyrrolo[2,3-d]pyrimidine ring. J. Heterocycl. Chem. (1969), -(2), 207-13.) (3.5 g). The solution was stirred at 65° C. for 16 hours and then partitioned between ethyl acetate and brine. The organic phase was separated, then dried over magnesium sulfate and then evaporated under reduced pressure. The residue was subjected to flash column chromatography on silica eluting with a mixture of ethyl acetate and cyclohexane (50:50, v/v) to give the title compound (1.2 g) as an amorphous solid. MS: 150 [MH]$^+$. LCMS (Method B) $R_T$=2.39 minutes.

REFERENCE EXAMPLE 9

4-(5-Methoxy-1-[(4-methylphenyl)sulfonyl]-1H-indol-3-yl)-6-(5-methoxy-1-methyl-1H-indol-3yl)-7-[(4-methylphenyl)sulfonyl]-7H-pyrrolo[2,3-d]pyrimidine To a solution of 4-(5-methoxy-1-[(4-methylphenyl)sulfonyl]-1H-indol-3-yl)-6-(5-methoxy-1H-indol-3-yl)-7-[(4-methylphenyl)sulfonyl]-7H-pyrrolo[2,3-d]pyrimidine [270 mg, Reference Example 10] in dimethylformamide (10 mL) was added the sodium hydride (10 mg, 60% dispersion in oil) and methyl iodide (0.025 mL) under inert atmosphere. The solution was stirred for 16 hours at room temperature and the solvent was evaporated under reduced pressure. The residue was partitioned between water and ethyl acetate The organic phase was separated, then dried over magnesium sulfate and then evaporated under reduced pressure. The residue was subjected to flash column chromatography on silica eluting with a mixture of ethyl acetate and cyclohexane (50:50, v/v) to give the title compound (93 mg) as an amorphous solid. MS: 732 [MH]$^+$. LCMS (Method B) $R_T$=4.68 minutes.

REFERENCE EXAMPLE 10

4-(5-Methoxy-1-[(4-methylphenyl)sulfonyl]-1H-indol-3-yl)-6-(5-methoxy-1H-indol-3-yl)-7-[(4-methylphenyl)sulfonyl]-7H-pyrrolo[2,3-d]pyrimidine A solution of 4-chloro-6-iodo-7-[(4-methylphenyl)sulfonyl]-7H-pyrrolo[2,3-d]pyrimidine [1.72 g, Reference Example 11] and 1-tert-butyl-carboxyl-5-methoxy-1H-indole-3-boronic acid [1.26 g, Reference Example 12] in dimethylformamide (36.5 mL) was treated successively with a saturated aqueous solution of sodium bicarbonate (9.1 mL) and palladium tetrakis triphenylphosphine (0.3 g). The reaction mixture was stirred at reflux for 2 hours and the solvent was evaporated under reduced pressure. The residue was partitioned between ethyl acetate and water. The organic phase was separated, then dried over magnesium sulfate and then evaporated under reduced pressure. The residue was subjected to flash column chromatography on silica eluting with a mixture of ethyl acetate and cyclohexane (30:70, v/v) to give the title compound (270 mg) as a gum. MS: 718 [MH]$^+$. LCMS (Method B) $R_T$=4.44 minutes.

REFERENCE EXAMPLE 11

4-Chloro-6-iodo-7-[(4-methylphenyl)sulfonyl]-7H-pyrrolo[2,3-d]pyrimidine

To a solution of 4-chloro-7-[(4-methylphenyl)sulfonyl]-7H-pyrrolo[2,3-d]pyrimidine [5.4 g, Reference Example 3], in tetrahydrofuran (96 mL) at −78° C. was added drop wise a solution of butyl lithium in hexane (12.1 mL, 1.6M) under inert atmosphere. The solution was stirred at −78° C. for 3 hours and iodine (8.9 g) was added. The reaction mixture was stirred at −78° C. for 2 hours, and allowed to reach room temperature. The reaction mixture was partitioned between ethyl acetate and aqueous sodium sulfite solution, dried over magnesium sulfate and the solvent was evaporated under reduced pressure. The residue was subjected to flash column chromatography on silica eluting with a gradient of ethyl acetate and cyclohexane (50:50, to 100, v/v) to give the title compound (1.52 g) as an amorphous solid. MS: 434 [MH]$^+$. LCMS (Method B) $R_T$=4.26 minutes.

REFERENCE EXAMPLE 12

1-tert-butyl-carboxyl-5-methoxy-1H-indole-3-boronic acid

A stirred solution of 3-bromo-5-methoxy-indole-1-carboxylic acid, tert-butyl ester [50 g, Reference Example 13] in tetrahydrofuran (800 mL), under nitrogen, was treated with tributylborate (49.5 mL) then cooled to −100° C. and then treated with a solution of n-butyllithium in hexanes (94 mL, 2.5M) whilst keeping the temperature below −90° C. Once the addition was complete the mixture was allowed, to warm slowly to room temperature over 1 hour and quenched by the addition of ice (10 g). The organics were removed under reduced pressure and the residue was partitioned between ethyl acetate (500 mL) and water (400 mL). The organic layer was dried over magnesium sulfate and then evaporated to afford the title compound as a cream coloured solid (28 g). MS: 314 [M+Na]$^+$. LCMS (Method C)$R_T$=4.07 minutes.

REFERENCE EXAMPLE 13

3-Bromo-5-methoxy-indole-1-carboxylic acid, tert-butyl ester

A solution of 5-methoxyindole (10 g) in dry dimethylformamide (150 mL) at ambient temperature was treated with bromine (4 mL) dropwise ensuring the temperature did not rise above 30° C. The mixture was treated immediately with triethylamine (28 mL) and 4-dimethylaminopyridine (0.5 g) followed by a solution of di-tert-butyldicarbonate (18 g) in dry dimethylformamide (80 mL) and stirring was continued for a further 4 hours. The reaction mixture was evaporated and the residue was partitioned between ethyl acetate (250 mL) and water (200 mL). The aqueous layer was extracted with ethyl acetate (100 mL). The combined organic phases were washed with water (100 mL), then with brine (100 mL), then dried over magnesium sulfate and then evaporated. The residue was subjected to flash column chromatography on silica eluting with a mixture of pentane and ethyl acetate (19/1, v/v) to give the title compound (23.4 g) as a colourless solid, m.p. 111-112° C.

In Vitro Test Procedures for SYK
 1. Inhibitory Effects of Compounds on Syk Kinase
 Inhibitory effects of compounds on Syk kinase were determined using a time-resolved fluorescent assay.
 The catalytic domain of Syk kinase (residues A340-N635) was expressed as a fusion protein in yeast cells and purified to homogeneity. Kinase activity was determined in 50 mM Tris-HCl buffer pH 7.0 containing 50 mM NaCl, 5 mM MgCl$_2$, 5 mM MnCl$_2$, 1 µM adenosine triphosphate and 10 µM synthetic peptide Biotin-(β-Alanine)$_3$-DEEDYEIPP-NH$_2$. Enzyme reactions were terminated by the addition of buffer containing 0.4M KF, 133 mM EDTA, pH 7.0, containing a streptavidin-XL665 conjugate and a monoclonal phosphospecfic antibody conjugated to a europium cryptate (Eu-K). Features of the two fluorophores, XL-665 and Eu-K are given in G. Mathis et al., Anticancer Research, 1997, 17, pages 3011-3014. The specific long time signal of XL-665, produced only when the synthetic peptide is phosphorylated by Syk, was measured on an LJL Biosystems Analyst AD microplate reader. Inhibition of syk activity with compounds of the invention was expressed as percentage inhibition of control activity exhibited in the absence of test compounds. Particular preferred compounds of the invention inhibit syk activity with IC$_{50}$s in the range 100 micromolar to 100 nanomolar. Especially preferred compounds of the invention inhibit syk activity with IC$_{50}$s in the range 1 micromolar to 100 nanomolar.

2. Antigen-Induced Degranulation of Rat Basophilic Leukemia (RBL) Cells
 2.1 Cell Culture, Labelling of RBL-2H3 Cells and Performance of Assay.
 RBL-2H3 cells are maintained in T75 flasks at 37° C. and 5% CO$_2$, and passaged every 3-4 days. To harvest cells, 5 ml trypsin-EDTA is used to rinse the flask once, then 5 ml trypsin is added to each flask, and incubated at room temperature for 2 minutes. Cells are transferred to a tube with 14 ml medium, spun down at 1100 rpm RT for 5 minutes and resuspended at 2×10$^5$/ml. Cells are sensitized by adding 1 µl of DNP-specific IgE to every 10 ml of cells. 200 µl of cells are added to each well of a flat-bottom 96 well plate (40,000 cells/well), and the plate incubated overnight at 37° C. and 5% CO$_2$. The next day compounds are prepared in 100% DMSO at 10 mM. Each compound is then diluted 1:100 in assay buffer and then diluted further in 1% DMSO-assay buffer to obtain final concentrations of 0.03-30 µM. 80 µl assay buffer is added to each well, followed by 10 µl of diluted compound. Incubation follows for 5 minutes. 10 µl of DNP-HSA (100 ng/ml) is added to each well and incubated at 37° C. (no CO$_2$) for 30 minutes. As one control, 1% DMSO alone (no compound) is added to a set of wells to determine total release. As another control, add buffer instead of DNP-HSA to another set of wells to determine the assay background. After the 30 minutes incubation, the supernatants are transferred to a new 96-well plate. Add 50 µl supernatant to each well of an assay plate. Add 100 µl of substrate solution to each well and incubate at 37° C. for 90 minutes. Add 50 µl of 0.4 M glycine solution to stop the reaction and the plate is read at 405 run on a Molecular Devices SpectraMax 250 plate reader.
 2.2 Calculation of Results
 (i) The mean±SD of each set of triplicate wells was calculated.
 (ii) Maximum response was the positive control wells containing antigen (100 ng/mL) but no compound.
 (iii) Minimum response was the control wells containing buffer (no antigen) and no compound.
 (iv) Using these values as the maximum (100%) and minimum (0%) values respectively, the experimental data was calculated to yield a percentage of the maximum response (designated % control).
 (v) A dose response curve was plotted and the IC$_{50}$ of the compound was calculated using Prism GraphPad software and nonlinear least squares regression analysis.
 Compounds of the invention inhibit antigen-induced degranulation of Rat Basophilic leukemia (RBL) cells with EC$_{50}$s in the range 100 micromolar to 1 micromolar.

What is claimed is:

1. A compound of the formula

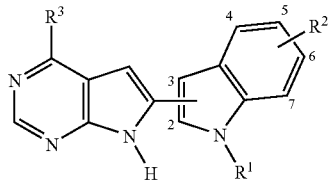

wherein

R¹ represents hydrogen, —C(=O)—NY¹Y², —C(=O)—OR⁵, —SO₂—NY¹Y², —SO₂—R⁷, —C(=O)R⁷, or R¹ represents alkenyl, alkenyloxy, alkyl, alkynyl, aryl, heteroaryl, heterocycloalkyl, cycloalkyl or cycloalkylalkyl, each optionally substituted by one or more groups selected from aryl, cycloalkyl, cyano, halo, heteroaryl, heterocycloalkyl, —CHO or a 5-, 6- or 7-membered cyclic acetal derivative of such —CHO, —C(=O)—NY¹Y², —C(=O)—OR⁵, —NY¹Y², —N(R⁶)—C(=O)—R⁷, —N(R⁶)—C(=O)—NY³Y⁴, —N(R⁶)—SO₂—R⁷, —N(R⁶)—SO₂—NY³Y⁴, —OR⁷, —C(=O)—R⁷, hydroxy, alkoxy and carboxy;

R² represents one or more groups selected from hydrogen, acyl, alkylenedioxy, alkenyl, alkenyloxy, alkynyl, aryl, cyano, halo, hydroxy, heteroaryl, heterocycloalkyl, nitro, R⁴, —C(=O)—NY¹Y², —C(=O)—OR⁵, —NY¹Y², —N(R⁶)—C(=O)—R⁷, —N(R⁶)—C(=O)—NY³Y⁴, —N(R⁶)—C(=O)—OR⁷, —N(R⁶)—SO₂—R⁷, —N(R⁶)—SO₂—NY³Y⁴, —SO₂—NY¹Y² and —ZR⁴;

R³ represents H, cyano, halo, hydroxy, nitro, R⁴, NY¹Y², —ZR⁴, —C(=O)—OR⁵, —C(=O)—R⁷, —C(=O)—NY¹Y², —N(R⁸)—C(=O)—R⁴, —N(R⁸)—C(=O)—NY¹Y², —N(R⁸)—C(=O)—OR⁵, —SO₂—NY³Y⁴, or —N(R⁸)—SO₂—R⁷, or R³ represents aryl, heteroaryl, alkenyl or alkynyl, each optionally substituted by one or more groups selected from aryl, cyano, halo, hydroxy, heteroaryl, heterocycloalkyl, nitro, —C(=O)—NY¹Y², —C(=O)—OR⁵, —NY¹Y², —N(R⁶)—C(=O)—R⁷, —N(R⁶)—C(=O)—NY³Y⁴, —N(R⁶)—C(=O)—OR⁷, —N(R⁶)—SO₂—R⁷, —N(R⁶)—SO₂—NY³Y⁴, —SO₂—NY¹Y² and —ZR⁴;

R⁴ represents alkyl, cycloalkyl or cycloalkylalkyl each optionally substituted by one or more groups selected from aryl, cycloalkyl, cyano, halo, heteroaryl, heterocycloalkyl, hydroxy, —CHO or a 5-, 6- or 7-membered cyclic acetal derivative of such —CHO, —C(=O)—NY¹Y², —C(=O)—OR⁵, —NY¹Y², —N(R⁶)—C(=O)—R⁷, —N(R⁶)—C(=O)—NY³Y⁴, —N(R⁶)—SO₂—R⁷, —N(R⁶)—SO₂—NY³Y⁴, —OR⁷ and —C(=O)—R⁷;

R⁵ represents hydrogen, alkyl, alkenyl, aryl, arylalkyl, heteroaryl or heteroarylalkyl;

R⁶ represents hydrogen or lower alkyl;

R⁷ represents alkyl, aryl, arylalkyl, cycloalkyl, cycloalkylalkyl, heteroaryl, heteroarylalkyl, heterocycloalkyl or heterocycloalkylalkyl;

R⁸ represents hydrogen or lower alkyl;

Y¹ and Y² are independently hydrogen, alkenyl, aryl, cycloalkyl, heteroaryl or alkyl optionally substituted by one or more groups selected from aryl, halo, heteroaryl, hydroxy, —C(=O)—NY³Y⁴, —C(=O)—OR⁵, —NY³Y⁴, —N(R⁶)—C(=O)—R⁷, —N(R⁶)—C(=O)—NY³Y⁴, —N(R⁶)—SO₂—R⁷, —N(R⁶)—SO₂—NY³Y⁴ and —OR⁷; or the group —NY¹Y² may form a cyclic amine;

Y³ and Y⁴ are independently hydrogen, alkenyl, alkyl, aryl, arylalkyl, cycloalkyl, heteroaryl or heteroarylalkyl; or the group —NY³Y⁴ may form a cyclic amine;

Z represents O or S(O)ₙ;

n is zero or an integer 1 or 2; or an N-oxide, an acid bioisostere selected from the group consisting of: —(C=O)—NHOH, —C(=O)—CH₂OH, —C(=O)—CH₂SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-doine, 3,5-dioxo-1,2,4-oxadiazolidinyl, 3-hydroxyisoxazolyl and 3-hydroxy-1-methylpyrazolyl; a pharmaceutically acceptable salt of such compound; or an N-oxide, or acid bioisostere selected from the group consisting of: —C(=O)—NHOH, —C(=O)—CH₂OH, —C(=O)—CH₂SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, 3-hydroxyisoxazolyl and 3-hydroxy-1-methylpyrazolyl; of such salt.

2. A compound according to claim 1 wherein

R¹ is hydrogen, $C_{1-4}$alkyl, $C_{1-4}$alkyl substituted by halo, $C_{1-4}$alkyl substituted by hydroxy, $C_{1-4}$alkyl substituted by —N(R⁶)C(=O)—R⁷, $C_{1-4}$alkyl substituted by —C(=O)—NY¹Y², or cycloalkylalkyl substituted by hydroxy.

3. A compound according to claim 1 wherein R¹ is hydrogen, —CH₃, —CH₂CH₃, —CH₂CF₃ or

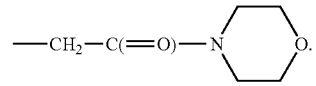

4. A compound according to claim 1 wherein R¹ is hydrogen.

5. A compound according to claim 1 wherein

R² is carboxy or an acid bioisostere selected from the group consisting of: —C(=O)—NHOH, —C(=O)—CH₂OH, —C(=O)—CH₂SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl, 3-hydroxyisoxazolyl and 3-hydroxy-1-methylpyrazolyl; hydroxy, alkyl substituted by carboxy, heteroaryl, or R² is —OR⁴ in which R⁴ is alkyl, —OR⁴ in which R⁴ is alkyl or cycloalkylalkyl substituted by one or more hydroxy groups, —OR⁴ in which R⁴ is alkyl substituted by one or more alkoxy groups, —OR⁴ in which R⁴ is alkyl or cycloalkyl substituted by one or more carboxy groups, —OR⁴ in which R⁴ is cycloalkyl substituted by —C(=O)—NY¹Y² or R² is —C(=O)—R in which R is alkyl, or R² is —C(=O)—NY¹Y², or —N(R⁶)—C(=O)—R⁷.

6. A compound according to claim 1 wherein R² is —OCH₃ or —CONHC(CH₃)₂CH₂OH.

7. A compound according to claim 1 wherein R² is —OCH₃.

8. A compound according to claim 1 wherein
R³ is hydrogen, cyano, optionally substituted aryl, optionally substituted heteroaryl, alkyl, alkyl substituted by one or more halogen atoms, alkyl substituted by —C(=O)—NY¹Y², alkyl substituted by —OR⁷, or R³ is —ZR⁴, —C(=O)—OR⁵, —C(=O)—NY¹Y², or —NY¹Y².

9. A compound according to claim 1 wherein R³ is hydrogen, cyano, pyridyl, trifluoromethyl, —CH₂—CH₂—C(=O)NHCH₃, —OCF₂H, —C(=O)—NH—C(CH₃)₂—CH₂OH or

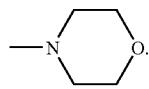

10. A compound according to claim 1 wherein R³ is —OCH₃.

11. A compound according to claim 1 wherein R² is attached at the 5-position of the indole ring.

12. A compound according to claim 1 wherein the group

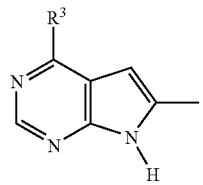

is attached to the 3-position of the indole ring.

13. A compound according to claim 1, which is selected from the group consisting of:

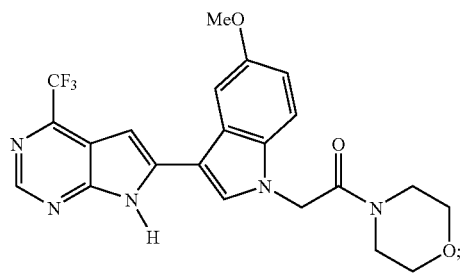

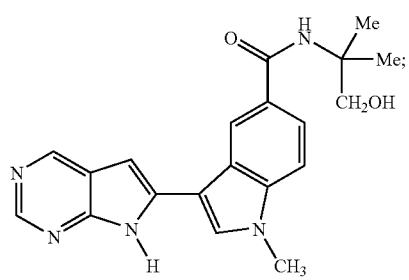

-continued

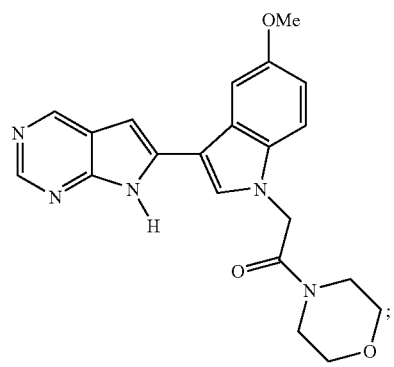

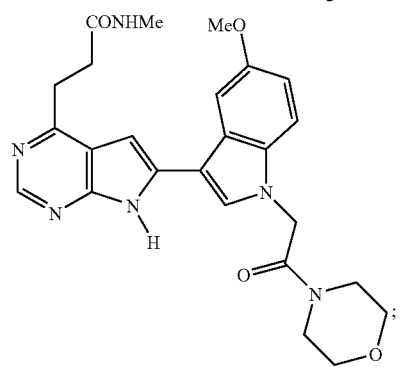

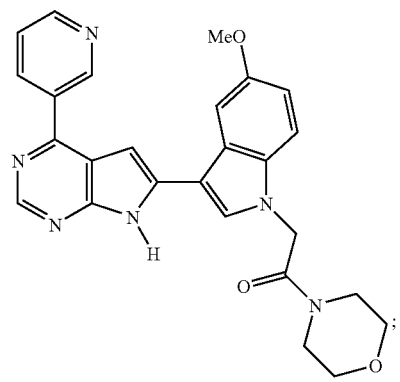

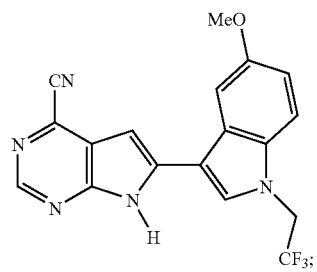

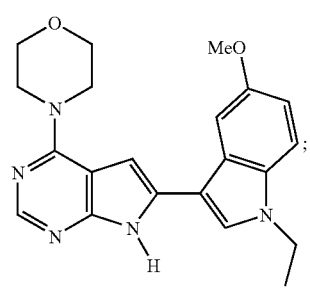

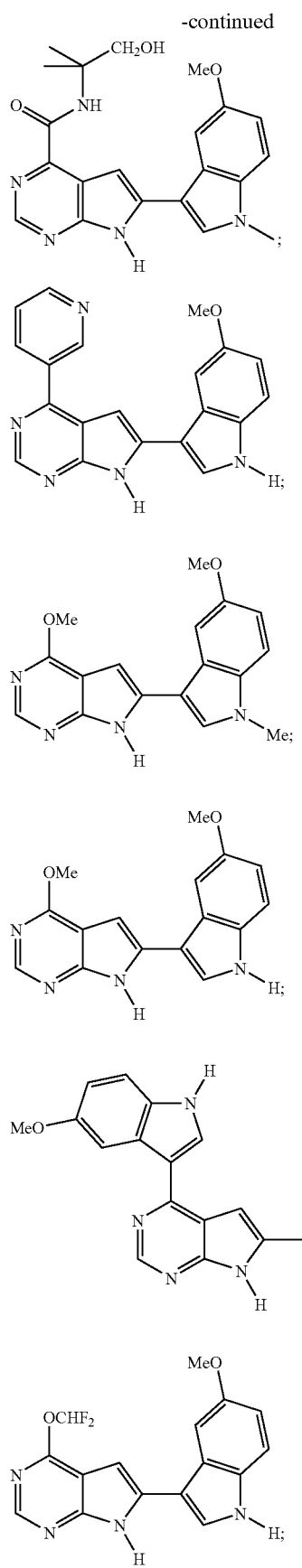
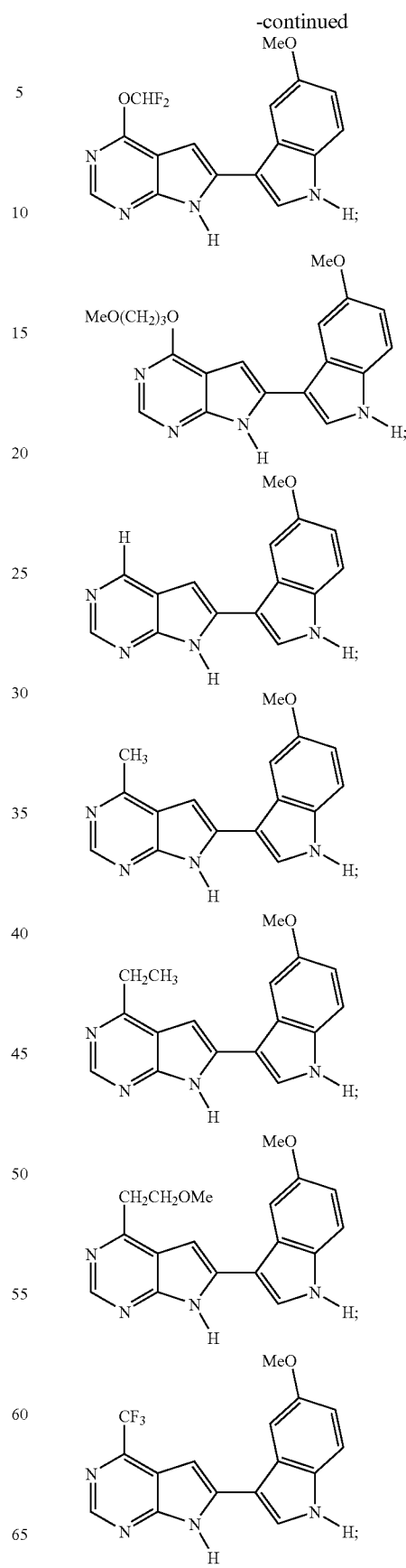

-continued

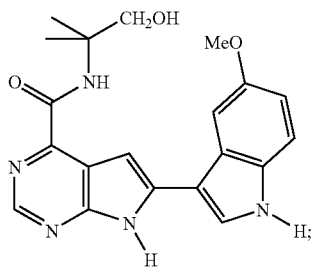

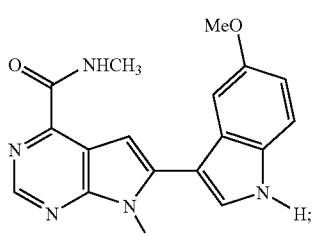

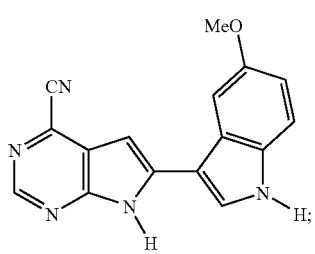

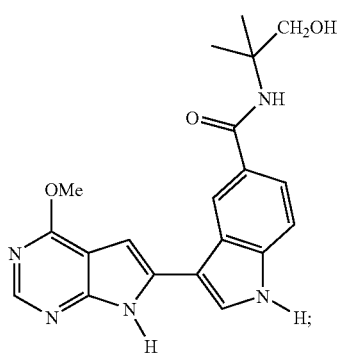

-continued

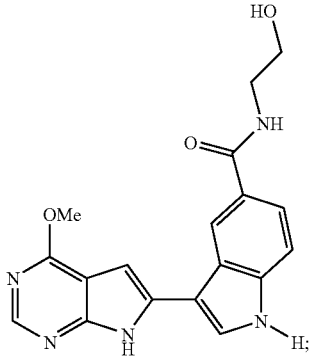

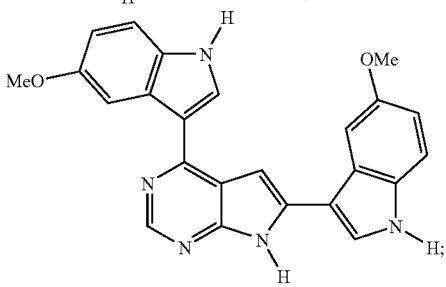

N-oxides, pharmaceutically acceptable salts of the above listed compounds; and N-oxides of said salts.

14. A compound according to claim 1 which is

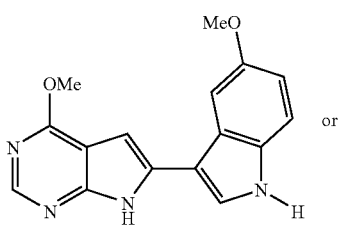 or an N-oxide, pharmaceutically acceptable salt of such compound; or an N-oxide of such salt.

15. A pharmaceutical composition comprising a pharmaceutically effective amount of a compound according to claim 1, together with one or more pharmaceutically acceptable carriers or excipients.

16. A method of treating asthma, comprising administering to a patient a pharmaceutically effective amount of a compound according to claim 1.

\* \* \* \* \*